United States Patent
Xu et al.

(10) Patent No.: US 12,364,651 B2
(45) Date of Patent: Jul. 22, 2025

(54) FLEXIBLE, POROUS, DISSOLVABLE SOLID SHEET ARTICLE CONTAINING DIRECT-ADDED MICROCAPSULES AND PROCESS FOR MAKING THE SAME

(71) Applicant: The Procter & Gamble Company, Cincinnati, OH (US)

(72) Inventors: Dan Xu, Beijing (CN); Carl David MacNamara, Beijing (CN); Xiao Tian, Beijing (CN); HongSing Tan, Beijing (CN); Robert Wayne Glenn, Jr., Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/394,446

(22) Filed: Aug. 5, 2021

(65) Prior Publication Data

US 2022/0054365 A1 Feb. 24, 2022

(30) Foreign Application Priority Data

Aug. 19, 2020 (WO) ................ PCT/CN2020/109963
Apr. 16, 2021 (WO) ................ PCT/CN2021/087782

(51) Int. Cl.
| | | |
|---|---|---|
| A61K 8/02 | (2006.01) |
| A61K 8/11 | (2006.01) |
| A61K 9/70 | (2006.01) |
| A61K 45/06 | (2006.01) |
| A61Q 19/00 | (2006.01) |
| C11D 3/20 | (2006.01) |
| C11D 3/22 | (2006.01) |
| C11D 3/30 | (2006.01) |
| C11D 3/37 | (2006.01) |
| C11D 3/50 | (2006.01) |
| C11D 17/06 | (2006.01) |

(52) U.S. Cl.
CPC ............ *A61K 8/0208* (2013.01); *A61K 8/11* (2013.01); *A61K 9/7007* (2013.01); *A61K 45/06* (2013.01); *A61Q 19/00* (2013.01); *C11D 3/2044* (2013.01); *C11D 3/222* (2013.01); *C11D 3/30* (2013.01); *C11D 3/3753* (2013.01); *C11D 3/505* (2013.01); *C11D 17/06* (2013.01); *A61K 2800/56* (2013.01); *A61K 2800/62* (2013.01)

(58) Field of Classification Search
None
See application file for complete search history.

(56) References Cited

U.S. PATENT DOCUMENTS

| | | |
|---|---|---|
| 3,293,718 A | 12/1966 | Melvin |
| 3,859,125 A | 1/1975 | Miller |
| 4,101,457 A | 7/1978 | Place |
| 4,170,565 A | 10/1979 | Flesher et al. |
| 4,180,558 A | 12/1979 | Franklin |
| 4,286,016 A | 8/1981 | Dimond |
| 4,287,219 A | 9/1981 | Fabre |
| 4,315,965 A | 2/1982 | Mason |
| 4,342,813 A | 8/1982 | Erickson |
| 4,349,531 A | 9/1982 | Mlodozeniec |
| 4,377,615 A | 3/1983 | Suzuki |
| 4,397,391 A | 8/1983 | Cornelissens |
| 4,415,617 A | 11/1983 | D Elia |
| 4,557,852 A | 12/1985 | Schulz et al. |
| 4,610,799 A | 9/1986 | Wilsberg et al. |
| 4,639,390 A | 1/1987 | Shoji |
| 4,654,395 A | 3/1987 | Schulz et al. |
| 4,743,394 A | 5/1988 | Kaufmann et al. |
| 4,747,976 A | 5/1988 | Yang et al. |
| 4,806,261 A | 2/1989 | Ciallella et al. |
| 4,892,758 A | 1/1990 | Serbiak |
| 4,923,660 A | 5/1990 | Willenberg |
| 4,938,888 A | 7/1990 | Kiefer et al. |
| 5,041,252 A | 8/1991 | Fujii |
| 5,110,678 A | 5/1992 | Narukawa |
| 5,120,888 A | 6/1992 | Nohr |
| 5,135,804 A | 8/1992 | Harpell |
| 5,158,810 A | 10/1992 | Oishi |
| 5,202,045 A | 4/1993 | Karpusiewicz et al. |
| 5,208,104 A | 5/1993 | Ueda |
| 5,230,853 A | 7/1993 | Colegrove |
| 5,246,603 A | 9/1993 | Tsaur |
| 5,342,335 A | 8/1994 | Rhim |
| 5,362,532 A | 11/1994 | Famili |
| 5,364,627 A | 11/1994 | Song |
| 5,387,147 A | 2/1995 | Ohshima |
| 5,429,874 A | 7/1995 | Vanputte |
| 5,455,114 A | 10/1995 | Ohmory |

(Continued)

FOREIGN PATENT DOCUMENTS

| | | |
|---|---|---|
| AU | 2004202461 B2 | 11/2007 |
| CA | 1242949 A | 10/1988 |

(Continued)

OTHER PUBLICATIONS

English translation of CN2019/122048 (2023).*
English translation of CN2019/071751 (2023).*
English translation of CN2019/076049 (2023).*
PCT Suppl. Search Report and Written Opinion for PCT/CN2021/087782 dated Dec. 7, 2022, 8 pages.
All Office Actions, U.S. Appl. No. 17/218,674.
PCT Search Report and Written Opinion for PCT/CN2020/109963 dated May 18, 2021, 14 pages.
PCT Search Report and Written Opinion for PCT/CN2021/087782 dated Jun. 29, 2021, 14 pages.
All Office Actions, U.S. Appl. No. 16/047,690, filed Jul. 27, 2018.
All Office Actions, U.S. Appl. No. 16/253,278, filed Jan. 22, 2019.

(Continued)

*Primary Examiner* — Patricia Duffy
*Assistant Examiner* — Garen Gotfredson
(74) *Attorney, Agent, or Firm* — Carolyn Powell; George H. Leal

(57) ABSTRACT

Flexible, dissolvable, porous solid sheet articles which include direct-added microcapsules therein for delivering a benefit agent and a process for making such solid sheet articles.

10 Claims, 3 Drawing Sheets

(56) References Cited

U.S. PATENT DOCUMENTS

| | | |
|---|---|---|
| 5,470,424 A | 11/1995 | Isaac |
| 5,470,653 A | 11/1995 | Honeycutt |
| 5,486,418 A | 1/1996 | Ohmory |
| 5,518,730 A | 5/1996 | Fuisz |
| 5,520,924 A | 5/1996 | Chapman |
| 5,538,735 A | 7/1996 | Ahn |
| 5,585,059 A | 12/1996 | Kobayashi |
| 5,651,987 A | 7/1997 | Fuisz |
| 5,691,015 A | 11/1997 | Tsukamoto |
| 5,705,183 A | 1/1998 | Phillips |
| 5,716,692 A | 2/1998 | Warner |
| 5,717,026 A | 2/1998 | Ikimine |
| 5,735,812 A | 4/1998 | Hardy |
| 5,780,418 A | 7/1998 | Niinaka |
| 5,827,586 A | 10/1998 | Yamashita |
| 5,840,423 A | 11/1998 | Sano |
| 5,863,887 A | 1/1999 | Gillette |
| 5,879,493 A | 3/1999 | Johnson |
| 5,911,224 A | 6/1999 | Berger |
| 5,914,124 A | 6/1999 | Mahoney |
| 5,942,179 A | 8/1999 | Tallentire |
| 6,008,181 A | 12/1999 | Cripe |
| 6,037,319 A | 3/2000 | Dickler |
| 6,066,396 A | 5/2000 | Inada |
| 6,080,346 A | 6/2000 | Jack |
| 6,130,193 A | 10/2000 | Gillette |
| 6,175,054 B1 | 1/2001 | Jacques |
| 6,197,238 B1 | 3/2001 | Wang |
| 6,207,274 B1 | 3/2001 | Ferenc |
| 6,274,162 B1 | 8/2001 | Steffenino |
| 6,319,510 B1 | 11/2001 | Yates |
| 6,406,797 B1 | 6/2002 | Vanputte |
| 6,420,625 B1 | 7/2002 | Jones |
| 6,440,911 B1 | 8/2002 | Bettiol et al. |
| 6,448,462 B2 | 9/2002 | Groitzsch |
| 6,465,407 B2 | 10/2002 | Hayashi |
| 6,552,123 B1 | 4/2003 | Katayama |
| 6,576,575 B2 | 6/2003 | Griesbach, III |
| 6,608,121 B2 | 8/2003 | Isozaki |
| 6,657,004 B2 | 12/2003 | Mizutani |
| 6,699,826 B1 | 3/2004 | Saijo |
| 6,730,648 B2 | 5/2004 | Gorlin |
| 6,783,852 B2 | 8/2004 | Inada |
| 6,787,512 B1 | 9/2004 | Verrall |
| 6,808,598 B1 | 10/2004 | Takeuchi |
| 6,818,606 B1 | 11/2004 | Hanada |
| 6,898,921 B2 | 5/2005 | Duffield |
| 6,949,498 B2 | 9/2005 | Murphy |
| 6,956,070 B2 | 10/2005 | Fujiwara |
| 6,977,116 B2 | 12/2005 | Cabell |
| 7,026,049 B2 | 4/2006 | Endo |
| 7,041,628 B2 | 5/2006 | Sunder |
| 7,067,575 B2 | 6/2006 | Kitamura |
| 7,083,047 B2 | 8/2006 | Bone |
| 7,094,744 B1 | 8/2006 | Kobayashi |
| 7,115,551 B2 | 10/2006 | Hasenoehrl |
| 7,169,740 B2 | 1/2007 | Sommerville-roberts |
| 7,196,026 B2 | 3/2007 | Di Luccio |
| RE39,557 E | 4/2007 | Moe |
| 7,226,899 B2 | 6/2007 | Cole |
| 7,285,520 B2 | 10/2007 | Krzysik |
| 7,387,787 B2 | 6/2008 | Fox |
| 7,407,669 B2 | 8/2008 | Leung |
| 7,429,273 B2 | 9/2008 | De Dominicis |
| 7,446,084 B2 | 11/2008 | Barthel |
| 7,491,407 B2 | 2/2009 | Pourdeyhimi |
| 7,507,698 B2 | 3/2009 | Franzolin |
| 7,547,737 B2 | 6/2009 | Kochvar |
| 7,563,757 B2 | 7/2009 | Kouvroukoglou |
| 7,708,840 B2 | 5/2010 | Wiedemann |
| 7,727,946 B2 | 6/2010 | Catalfamo |
| 7,824,588 B2 | 11/2010 | Yang |
| 7,856,989 B2 | 12/2010 | Karles |
| 7,967,801 B2 | 6/2011 | Hammons |
| 8,288,332 B2 | 10/2012 | Fossum et al. |
| 8,338,358 B2 | 12/2012 | Bernhardt |
| 8,349,232 B2 | 1/2013 | Pourdeyhimi |
| 8,367,596 B2 | 2/2013 | Fossum et al. |
| 8,785,361 B2 | 7/2014 | Sivik |
| 8,980,816 B2 | 3/2015 | Dreher |
| 9,074,305 B2 | 7/2015 | Glenn, Jr. |
| 9,163,205 B2 | 10/2015 | Sivik |
| 9,175,250 B2 | 11/2015 | Sivik |
| 9,267,095 B2 | 2/2016 | Delaney |
| 9,421,153 B2 | 8/2016 | Sivik |
| 9,480,628 B2 | 11/2016 | Sivik |
| 9,493,726 B2 | 11/2016 | Vinson |
| 9,796,948 B2 | 10/2017 | Shearouse |
| 10,045,915 B2 | 8/2018 | Glenn, Jr. |
| 10,683,618 B2 | 6/2020 | Pratt et al. |
| 10,857,756 B2 | 12/2020 | Pratt et al. |
| 2001/0037851 A1 | 11/2001 | Mortellite |
| 2002/0013251 A1 | 1/2002 | Hayashi |
| 2002/0018906 A1 | 2/2002 | Clark |
| 2002/0032142 A1 | 3/2002 | Smets et al. |
| 2002/0091169 A1 | 7/2002 | Klotzer |
| 2002/0098994 A1 | 7/2002 | Zafar |
| 2002/0161088 A1 | 10/2002 | Kochvar |
| 2002/0173213 A1 | 11/2002 | Chu |
| 2003/0017208 A1 | 1/2003 | Ignatious |
| 2003/0045446 A1 | 3/2003 | Dihora |
| 2003/0166495 A1 | 9/2003 | Wang |
| 2003/0185872 A1 | 10/2003 | Kochinke |
| 2003/0216098 A1 | 11/2003 | Carlyle |
| 2003/0224959 A1 | 12/2003 | Smith |
| 2004/0129032 A1 | 7/2004 | Severns |
| 2004/0129597 A1 | 7/2004 | Fregonese |
| 2004/0167256 A1 | 8/2004 | Verrall |
| 2004/0170836 A1 | 9/2004 | Bond |
| 2004/0180597 A1 | 9/2004 | Kamada |
| 2004/0204543 A1 | 10/2004 | Yang |
| 2005/0003048 A1 | 1/2005 | Pearce |
| 2005/0003980 A1 | 1/2005 | Baker |
| 2005/0003991 A1 | 1/2005 | Macquarrie |
| 2005/0008776 A1 | 1/2005 | Chhabra |
| 2005/0010010 A1 | 1/2005 | Kitamura |
| 2005/0136112 A1 | 6/2005 | Gonzales |
| 2005/0136780 A1 | 6/2005 | Clark et al. |
| 2005/0186256 A1 | 8/2005 | Dihel |
| 2005/0209574 A1 | 9/2005 | Boehringer |
| 2005/0266542 A1 | 12/2005 | Baur et al. |
| 2005/0281757 A1 | 12/2005 | Ibrahim |
| 2006/0013869 A1 | 1/2006 | Ignatious |
| 2006/0035042 A1 | 2/2006 | Morken |
| 2006/0083784 A1 | 4/2006 | Ignatious |
| 2006/0111261 A1 | 5/2006 | Sadlowski |
| 2006/0127458 A1 | 6/2006 | Kiser |
| 2006/0134412 A1 | 6/2006 | Mackey |
| 2006/0160453 A1 | 7/2006 | Suh |
| 2006/0189772 A1 | 8/2006 | Scheibel |
| 2006/0205628 A1 | 9/2006 | Deinhammer |
| 2006/0254013 A1 | 11/2006 | Konishi |
| 2006/0254014 A1 | 11/2006 | Konishi |
| 2006/0258251 A1 | 11/2006 | Konishi |
| 2006/0264130 A1 | 11/2006 | Karles |
| 2007/0054579 A1 | 3/2007 | Baker, Jr. |
| 2007/0110792 A9 | 5/2007 | Simon |
| 2007/0128256 A1 | 6/2007 | Aubrun-sonneville |
| 2007/0134304 A1 | 6/2007 | Aubrun-sonneville |
| 2007/0134481 A1 | 6/2007 | Aubrun-sonneville |
| 2007/0253926 A1 | 11/2007 | Tadrowski |
| 2007/0259170 A1 | 11/2007 | Brown |
| 2007/0259996 A1 | 11/2007 | Vicari |
| 2007/0281874 A1 | 12/2007 | Frankenbach |
| 2007/0298064 A1 | 12/2007 | Koslow |
| 2008/0035174 A1 | 2/2008 | Aubrun-sonneville |
| 2008/0108748 A1 | 5/2008 | Buckley |
| 2008/0118727 A1 | 5/2008 | Andersen |
| 2008/0146481 A1 | 6/2008 | Brown |
| 2008/0149119 A1 | 6/2008 | Shen |
| 2008/0220054 A1 | 9/2008 | Shastri |
| 2008/0226919 A1 | 9/2008 | Hosoda |
| 2008/0242572 A1 | 10/2008 | Icht |
| 2008/0269095 A1 | 10/2008 | Aubrun-sonneville |

(56) References Cited

U.S. PATENT DOCUMENTS

| | | |
|---|---|---|
| 2009/0004254 A1 | 1/2009 | Maibach |
| 2009/0041820 A1 | 2/2009 | Wu et al. |
| 2009/0061496 A1 | 3/2009 | Kuhn |
| 2009/0061719 A1 | 3/2009 | Shibutani |
| 2009/0104420 A1 | 4/2009 | Nadella et al. |
| 2009/0155326 A1 | 6/2009 | Mack |
| 2009/0181587 A1 | 7/2009 | Kang |
| 2009/0249558 A1 | 10/2009 | Fileccia |
| 2009/0285718 A1 | 11/2009 | Privitera |
| 2009/0291282 A1 | 11/2009 | Kitamura et al. |
| 2010/0018641 A1 | 1/2010 | Branham |
| 2010/0021517 A1 | 1/2010 | Ahlers |
| 2010/0105821 A1 | 4/2010 | Verrall |
| 2010/0166854 A1 | 7/2010 | Michniak-kohn |
| 2010/0179083 A1 | 7/2010 | Glenn, Jr. et al. |
| 2010/0196440 A1 | 8/2010 | Stark |
| 2010/0266668 A1 | 10/2010 | Coffee |
| 2010/0279905 A1 | 11/2010 | Glenn, Jr. |
| 2010/0285101 A1 | 11/2010 | Moore |
| 2010/0286011 A1 | 11/2010 | Glenn, Jr. et al. |
| 2010/0298188 A1 | 11/2010 | Glenn, Jr. et al. |
| 2011/0023240 A1* | 2/2011 | Fossum .................. C11D 3/222 510/331 |
| 2011/0065163 A1 | 3/2011 | Vaha-vahe |
| 2011/0111999 A1* | 5/2011 | Smets .................... C11D 3/505 510/516 |
| 2011/0136719 A1 | 6/2011 | Jalbert |
| 2011/0159267 A1 | 6/2011 | Lee |
| 2011/0223381 A1 | 9/2011 | Sauter |
| 2011/0230112 A1 | 9/2011 | Rose |
| 2011/0301070 A1 | 12/2011 | Ochomogo |
| 2012/0021026 A1 | 1/2012 | Glenn, Jr. |
| 2012/0027838 A1 | 2/2012 | Gordon |
| 2012/0041029 A1 | 2/2012 | Srinivas et al. |
| 2012/0048769 A1 | 3/2012 | Sivik |
| 2012/0052036 A1 | 3/2012 | Glenn, Jr. |
| 2012/0053103 A1 | 3/2012 | Sivik |
| 2012/0053108 A1 | 3/2012 | Glenn, Jr. |
| 2012/0058166 A1 | 3/2012 | Glenn, Jr. |
| 2012/0082037 A1 | 4/2012 | Wang |
| 2012/0154300 A1 | 6/2012 | Ma |
| 2012/0172831 A1 | 7/2012 | Darcy |
| 2012/0215148 A1 | 8/2012 | Ewert |
| 2012/0237576 A1 | 9/2012 | Gordon |
| 2013/0167305 A1 | 7/2013 | Weisman et al. |
| 2013/0171421 A1 | 7/2013 | Weisman et al. |
| 2013/0172226 A1 | 7/2013 | Dreher et al. |
| 2014/0073551 A1 | 3/2014 | Mort, III et al. |
| 2014/0287973 A1 | 9/2014 | Sivik |
| 2014/0366294 A1 | 12/2014 | Roe |
| 2015/0048001 A1 | 2/2015 | Bailey |
| 2015/0104856 A1 | 4/2015 | Astrid |
| 2015/0159330 A1 | 6/2015 | Weisman et al. |
| 2015/0218497 A1 | 8/2015 | Jalbert et al. |
| 2015/0313807 A1 | 11/2015 | Lynch |
| 2015/0368001 A1 | 12/2015 | Gruenbacher |
| 2016/0010041 A1 | 1/2016 | Sivik |
| 2016/0024447 A1 | 1/2016 | Simonsen et al. |
| 2016/0040105 A1 | 2/2016 | Depoot et al. |
| 2016/0101204 A1 | 4/2016 | Lynch |
| 2016/0137956 A1 | 5/2016 | Hayward et al. |
| 2016/0152927 A1 | 6/2016 | Van Deurzen |
| 2016/0186095 A1 | 6/2016 | Vockenroth |
| 2016/0200501 A1 | 7/2016 | Lee |
| 2016/0250109 A1 | 9/2016 | Dreher et al. |
| 2016/0271021 A1 | 9/2016 | Glenn, Jr. |
| 2016/0340624 A1 | 11/2016 | Sivik |
| 2016/0374906 A1 | 12/2016 | Sivik |
| 2017/0009191 A1 | 1/2017 | Maes |
| 2017/0067002 A1 | 3/2017 | Cumming |
| 2017/0096354 A1 | 4/2017 | Li |
| 2017/0164612 A1 | 6/2017 | Ripberger |
| 2017/0320105 A1 | 11/2017 | Roozrokh |
| 2018/0215053 A1 | 8/2018 | Miller |
| 2018/0216050 A1 | 8/2018 | Denome |
| 2018/0216052 A1 | 8/2018 | Denome |
| 2018/0216053 A1 | 8/2018 | Denome |
| 2018/0216286 A1 | 8/2018 | Glassmeyer |
| 2018/0216287 A1 | 8/2018 | Weisman |
| 2018/0218286 A1 | 8/2018 | Predovic |
| 2018/0223225 A1* | 8/2018 | Tan ........................ C11D 3/222 |
| 2018/0223229 A1 | 8/2018 | Tan |
| 2018/0338890 A1 | 11/2018 | Glenn, Jr. |
| 2019/0233782 A1 | 8/2019 | Sivik |
| 2019/0233783 A1 | 8/2019 | Sivik |
| 2019/0233784 A1 | 8/2019 | Sivik |
| 2019/0233785 A1 | 8/2019 | Sivik |
| 2020/0032179 A1 | 1/2020 | Sivik |
| 2020/0190433 A1 | 6/2020 | Nyangiro et al. |
| 2021/0163698 A1* | 6/2021 | MacNamara .......... C08J 9/0033 |
| 2021/0238513 A1 | 8/2021 | Sivik et al. |
| 2021/0261892 A1* | 8/2021 | Xu ......................... A61K 8/416 |
| 2021/0332212 A1* | 10/2021 | Tan ........................ A61K 8/463 |
| 2021/0332312 A1 | 10/2021 | Tan et al. |

FOREIGN PATENT DOCUMENTS

| | | |
|---|---|---|
| CA | 2695068 A1 | 9/2010 |
| CN | 1202517 A | 12/1998 |
| CN | 1222186 A | 7/1999 |
| CN | 2352536 Y | 12/1999 |
| CN | 1250085 A | 4/2000 |
| CN | 1421519 A | 6/2003 |
| CN | 1426458 A | 6/2003 |
| CN | 1474657 A | 2/2004 |
| CN | 1583991 A | 2/2005 |
| CN | 1751116 A | 3/2006 |
| CN | 202744521 U | 2/2013 |
| CN | 202754982 U | 2/2013 |
| CN | 102492573 B | 4/2013 |
| CN | 102732392 B | 9/2013 |
| CN | 102965223 B | 1/2014 |
| CN | 103740490 A | 4/2014 |
| CN | 105199887 A | 12/2015 |
| CN | 105238584 A | 1/2016 |
| CN | 105462733 A | 4/2016 |
| CN | 105586165 A | 5/2016 |
| CN | 105602773 A | 5/2016 |
| CN | 105647716 A | 6/2016 |
| CN | 205398584 U | 7/2016 |
| CN | 105861168 A | 8/2016 |
| CN | 105886142 A | 8/2016 |
| CN | 205420320 U | 8/2016 |
| CN | 106635572 A | 5/2017 |
| CN | 107075416 A | 8/2017 |
| CN | 107709532 A | 2/2018 |
| CN | 108822976 A | 11/2018 |
| DE | 102007011606 A1 | 9/2008 |
| EP | 0234867 B1 | 1/1993 |
| EP | 1275368 A1 | 1/2003 |
| EP | 1306425 A2 | 5/2003 |
| EP | 1409628 B1 | 2/2006 |
| EP | 1512701 B1 | 6/2006 |
| EP | 1887036 A2 | 2/2008 |
| EP | 1436376 B1 | 4/2010 |
| EP | 2226379 A1 | 9/2010 |
| EP | 1948771 B1 | 12/2010 |
| EP | 2319965 A1 | 5/2011 |
| EP | 2363432 A1 | 9/2011 |
| EP | 2363517 A1 | 9/2011 |
| EP | 2395142 A1 | 12/2011 |
| GB | 2107579 A | 5/1983 |
| GB | 2375542 A | 11/2002 |
| GB | 2449418 B | 11/2010 |
| HU | 221299 B1 | 9/2002 |
| JP | 62156348 | 7/1987 |
| JP | S638496 A | 1/1988 |
| JP | S6312466 A | 3/1988 |
| JP | S63150396 A | 6/1988 |
| JP | H0340879 A | 2/1991 |
| JP | H03101618 A | 4/1991 |
| JP | H04202600 A | 7/1992 |
| JP | H0569758 B2 | 3/1993 |
| JP | 09279457 | 10/1997 |

(56) References Cited

FOREIGN PATENT DOCUMENTS

| | | |
|---|---|---|
| JP | 10008364 A | 1/1998 |
| JP | H108098 A | 1/1998 |
| JP | H108364 A | 1/1998 |
| JP | 10158700 A | 6/1998 |
| JP | H1121594 A | 1/1999 |
| JP | H11124600 A | 5/1999 |
| JP | 2000169896 A | 6/2000 |
| JP | 2001294899 A | 10/2001 |
| JP | 2006517989 A | 8/2006 |
| JP | 2009079329 A | 4/2009 |
| JP | 4509284 B2 | 5/2010 |
| JP | 2016540701 A | 12/2016 |
| JP | 2017514852 A | 6/2017 |
| JP | 2017530268 A | 10/2017 |
| KR | 20080111815 A | 12/2008 |
| KR | 20090036882 A | 4/2009 |
| KR | 20090036883 A | 4/2009 |
| KR | 20100090122 A | 8/2010 |
| KR | 20100096985 A | 9/2010 |
| KR | 101146292 B1 | 5/2012 |
| KR | 20120127174 A | 11/2012 |
| KR | 20120130693 A | 12/2012 |
| WO | 9206603 A1 | 4/1992 |
| WO | 1992006603 A1 | 4/1992 |
| WO | 9402377 A1 | 2/1994 |
| WO | 9404656 A2 | 3/1994 |
| WO | 9523888 A1 | 9/1995 |
| WO | 9739087 A1 | 10/1997 |
| WO | 9957155 A1 | 11/1999 |
| WO | 0013680 A2 | 3/2000 |
| WO | 0027958 A1 | 5/2000 |
| WO | 0125322 A1 | 4/2001 |
| WO | 0154667 A1 | 8/2001 |
| WO | 200154667 A1 | 8/2001 |
| WO | 03060007 A1 | 7/2003 |
| WO | 2004009335 A1 | 1/2004 |
| WO | 2004081162 A1 | 9/2004 |
| WO | 2005068604 A1 | 7/2005 |
| WO | 2006106514 A2 | 10/2006 |
| WO | 2007089259 A1 | 8/2007 |
| WO | 2007093558 A3 | 1/2008 |
| WO | 2009022761 A1 | 2/2009 |
| WO | 2007014221 A3 | 4/2009 |
| WO | 2009047124 | 4/2009 |
| WO | 2009047127 A1 | 4/2009 |
| WO | 2009095891 A1 | 8/2009 |
| WO | 2009103576 A1 | 8/2009 |
| WO | 2009121900 A1 | 10/2009 |
| WO | 2009129358 A2 | 10/2009 |
| WO | 2010015709 A2 | 2/2010 |
| WO | 2010135238 A1 | 11/2010 |
| WO | 2011153023 A1 | 12/2011 |
| WO | 2012003367 A3 | 3/2012 |
| WO | 2012138820 A1 | 10/2012 |
| WO | 2012157851 A2 | 11/2012 |
| WO | 2014032269 A1 | 3/2014 |
| WO | 2014059252 A3 | 12/2014 |
| WO | 2016172088 A1 | 10/2016 |
| WO | 2017096354 A1 | 6/2017 |
| WO | 2017184606 A2 | 10/2017 |
| WO | 2018075834 A1 | 4/2018 |
| WO | 2018141096 A1 | 8/2018 |
| WO | 2020147010 A1 | 7/2020 |
| WO | 2020233189 A1 | 11/2020 |

OTHER PUBLICATIONS

Makadia, et al., In Journal of Polymers vol. 3, Issue 3, 2011, pp. 1377-1397.

Smith, et al., In Journal of Nanotechnologies for the Life Sciences, vol. 9, 2006, pp. 188-215.

Wang, et al., In Journal of Pharmaceutical Sciences, vol. 99, Issue, dated Dec. 12, 2010, pp. 4805-4811.

* cited by examiner

FLEXIBLE, POROUS, DISSOLVABLE SOLID SHEET ARTICLE CONTAINING DIRECT-ADDED MICROCAPSULES AND PROCESS FOR MAKING THE SAME

FIELD OF THE INVENTION

The present disclosure relates to flexible, porous, dissolvable solid articles containing direct-added microcapsules therein for delivering a benefit agent, and a process for making the same.

BACKGROUND OF THE INVENTION

Flexible and dissolvable sheets comprising surfactant(s) and/or other active ingredients in a water-soluble polymeric carrier or matrix are well known. Such sheets are particularly useful for delivering surfactants and/or other active ingredients upon dissolution in water. In comparison with traditional granular or liquid forms in the same product category, such sheets have better structural integrity, are more concentrated and easier to store, ship/transport, carry, and handle. In comparison with the solid tablet form in the same product category, such sheets are more flexible and less brittle, with better sensory appeal to the consumers.

It is particularly desirable to use such flexible and dissolvable sheets to deliver long-lasting freshness (e.g., scent that lasts for several days) or other sensorial or functional benefits to consumers. Long-lasting freshness can be achieved by various mechanisms, among which perfume microcapsules (PMCs) are becoming increasingly more popular. For example, WO2018141096 discloses a process for incorporating PMCs into a flexible and dissolvable sheet, after such sheet is formed (instead of incorporating said friable microcapsules into the original starting materials used for forming such sheet). Similarly, WO2011014643, which discloses formation of flexible and dissolvable sheets with open-celled foam (OCF) structures therein to further improve dissolution thereof, teaches in its Examples 13 and 14 the addition of PMCs by spraying a slurry containing such microcapsules onto a porous sheet that has already been formed. It was believed that the PMCs, being friable in nature, may rapture or break under the heat, pressure and/or shear force applied during the sheet-forming process to pre-maturely release the perfumes encapsulated therein. Therefore, WO20181411096A and WO2011014643 disclose post sheet-forming addition of PMCs (i.e., "Post-Added" PMCs), which may help to preserve the structural integrity of such microcapsules and minimize pre-mature rapture/breakage of the microcapsules.

However, severe gelling issue has been observed in the flexible and dissolvable sheets containing Post-Added PMCs, especially when such sheets contain OCF structures therein. Without being bound by any theory, it is believed that because the PMCs are provided in a slurry form (which contains a significant amount of water), excessive water in the PMC-containing slurry may incidentally dissolve a portion of the sheets that first comes into contact with the slurry, resulting in collapse of the OCF structures and formation of a slow-dissolving gel layer in said portion. The gelling issue can be further exacerbated when multiple layers of such flexible and dissolvable sheets are assembled together to form a multilayer structure for delivering the required dosage of surfactants/actives for one wash cycle or one cleaning need. As a result, such multilayer structure may not completely dissolve, especially when it is exposed to certain stringent washing conditions (e.g., cold water or extremely hard water, or low water washing conditions), to leave undissolved residues that can become a big consumer "pain point".

Correspondingly, there is a need for improving the dissolution profile and reducing gelling of flexible and dissolvable sheets containing OCF structures therein with PMCs and/or other actives-containing microcapsules, while still enabling effective delivery of long-lasting freshness and/or other sensorial/functional benefits to consumers.

SUMMARY OF THE INVENTION

It is a surprising and unexpected discovery of the present disclosure that the dissolution profile of the above-mentioned flexible and dissolvable sheets can be significantly improved, and the gelling issue effectively reduced, while still enabling effective delivery of long-lasting freshness and/or other sensorial/functional benefits to consumers, by directly adding the slurry containing PMCs and/or other actives-containing microcapsules (i.e., "Direct-Added" PMCs or other microcapsules) into the wet pre-mixture before the aeration, sheet-forming and drying steps to make the flexible and dissolvable sheets. Contrary to conventional wisdom, the present disclosure finds that the aeration, sheet-forming and drying steps do not cause significant damage to the PMCs and/or other actives-containing microcapsules, and a majority of such Direct-Added PMCs and/or other actives-containing microcapsules are able to survive such processing steps intact and to deliver the desired long-lasting freshness and/or other sensorial/functional benefits. Without being bound by any theory, it is believed that the viscous wet pre-mixture and the air bubbles generated during the aeration step function in combination to suspend and protect the PMCs and/or other actives-containing microcapsules against external pressure or force. Further, the subsequent drying step removes excessive water introduced by the slurry containing PMCs and/or other actives-containing microcapsules at well-controlled temperatures, thereby on one hand preventing such water from dissolving/damaging OCF structures and causing gelling issue in the resulting solid sheet article, and on the other hand avoiding overheating that may rapture/break the PMCs.

In one aspect, the present disclosure is related to a process for preparing a solid sheet article, comprising the steps of:
 a) providing a wet pre-mixture comprising a water-soluble polymer, a surfactant and microcapsules, wherein said wet pre-mixture has a viscosity of from 1,000 cps to 25,000 cps measured at 40° C. and 1 s−1, wherein each of said microcapsules comprises a core and a shell at least partially surrounding the core, and wherein the core comprises a benefit agent; and
 b) aerating said wet pre-mixture to form an aerated wet pre-mixture having a density of from 0.05 to 0.5 g/ml; and
 c) forming said aerated wet pre-mixture into a sheet; and
 d) drying said formed sheet for a drying time of from 1 minute to 60 minutes at a temperature from 70° C. to 200° C. to form said solid sheet article.

In another aspect, the present disclosure is related to a flexible, porous, dissolvable solid sheet article comprising a water-soluble polymer, a surfactant, and a plurality of microcapsules; wherein said solid sheet article has opposing first and second planar surfaces; wherein each of said plurality of microcapsules comprises a core and a shell at least partially surrounding the core, and wherein the core comprises a benefit agent; wherein at least one of said microcapsules is located between said opposing first and second planar surfaces; and wherein said solid sheet article is characterized by: (i) a Percent Open Cell Content of from 80% to 100%; and (ii) an Overall Average Pore Size of from 100 μm to 2000 μm. Preferably, a majority of said plurality of microcapsules are located between said opposing first and second planar surfaces of the solid sheet article.

In another aspect, the present disclosure is related to a multilayer structure comprising two or more layers of the flexible, porous, dissolvable solid sheet article as described hereinabove.

These and other aspects of the present disclosure will become more apparent upon reading the following detailed description.

DETAILED DESCRIPTION OF THE INVENTION

I. Definitions

Figure 1A:
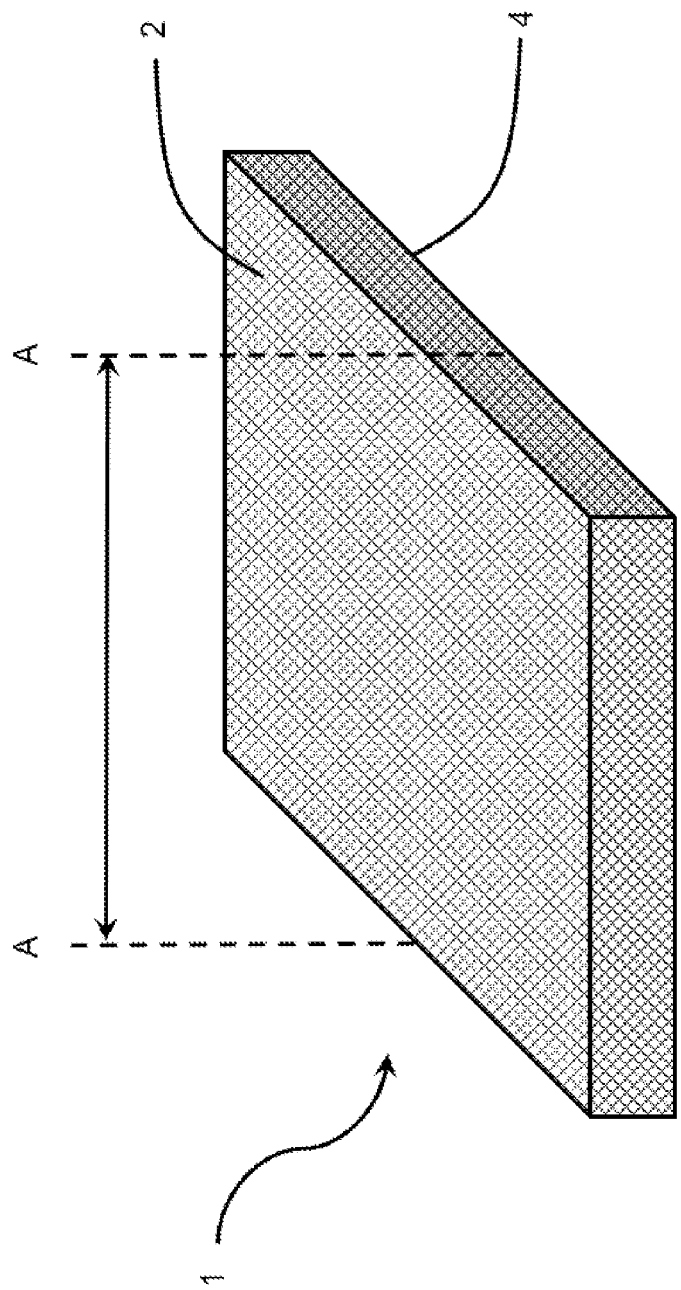
FIG. 1A is a schematic view of an exemplary flexible, porous, dissolvable solid sheet article according to the present disclosure.

The term "flexible" as used herein refers to the ability of an article to withstand stress without breakage or significant fracture when it is bent at 900 along a center line perpendicular to its longitudinal direction. Preferably, such article can undergo significant elastic deformation and is characterized by a Young's Modulus of no more than 5 GPa, preferably no more than 1 GPa, more preferably no more than 0.5 GPa, most preferably no more than 0.2 GPa.

The term "dissolvable" as used herein refers to the ability of an article to completely or substantially dissolve in a sufficient amount of deionized water at 20° C. and under the atmospheric pressure within eight (8) hours without any stirring, leaving less than 5 wt % undissolved residues.

The term "solid" as used herein refers to the ability of an article to substantially retain its shape (i.e., without any visible change in its shape) at 20° C. and under the atmospheric pressure, when it is not confined and when no external force is applied thereto.

The term "sheet" as used herein refers to a non-fibrous structure having a three-dimensional shape, i.e., with a thickness, a length, and a width, while the length-to-thickness aspect ratio and the width-to-thickness aspect ratio are both at least about 5:1, and the length-to-width ratio is at least about 1:1. Preferably, the length-to-thickness aspect ratio and the width-to-thickness aspect ratio are both at least about 10:1, more preferably at least about 15:1, most preferably at least about 20:1; and the length-to-width aspect ratio is preferably at least about 1.2:1, more preferably at least about 1.5:1, most preferably at least about 1.618:1.

The term "water-soluble" as used herein refers to the ability of a sample material to completely dissolve in or disperse into water leaving no visible solids or forming no visibly separate phase, when at least about 25 grams, preferably at least about 50 grams, more preferably at least about 100 grams, most preferably at least about 200 grams, of such material is placed in one liter (1 L) of deionized water at 20° C. and under the atmospheric pressure with sufficient stirring.

The term "aerate", "aerating" or "aeration" as used herein refers to a process of introducing a gas into a liquid or pasty composition by mechanical and/or chemical means.

The term "open celled foam" or "open cell pore structure" as used herein refers to a solid, interconnected, polymer-containing matrix that defines a network of spaces or cells that contain a gas, typically a gas (such as air), without collapse of the foam structure during the drying process, thereby maintaining the physical strength and cohesiveness of the solid. The interconnectivity of the structure may be described by a Percent Open Cell Content, which is measured by Test 3 disclosed hereinafter.

The term "essentially free of" or "essentially free from" means that the indicated material is at the very minimal not deliberately added to the composition or product, or preferably not present at an analytically detectable level in such composition or product. It may include compositions or products in which the indicated material is present only as an impurity of one or more of the materials deliberately added to such compositions or products.

As used herein, the term "bottom surface" refers to a surface of the flexible, porous, dissolvable solid sheet of the present disclosure that is immediately contacting a supporting surface upon which the sheet of aerated wet pre-mixture is placed during the drying step, while the term "top surface" refers to a surface of the sheet that is opposite to the bottom surface. Further, such solid sheet can be divided into three (3) regions along its thickness, including a top region that is adjacent to its top surface, a bottom region that is adjacent to its bottom surface, and a middle region that is located between the top and bottom regions. The top, middle, and bottom regions are of equal thickness, i.e., each having a thickness that is about ⅓ of the total thickness of the sheet.

The term "heating direction" as used herein refers to the direction along which a heat source applies thermal energy to an article, which results in a temperature gradient in such article that decreases from one side of such article to the other side. For example, if a heat source located at one side of the article applies thermal energy to the article to generate a temperature gradient that decreases from the one side to an opposing side, the heating direction is then deemed as extending from the one side to the opposing side. If both sides of such article, or different sections of such article, are heated simultaneously with no observable temperature gradient across such article, then the heating is carried out in a non-directional manner, and there is no heating direction.

The term "substantially opposite to" or "substantially offset from" as used herein refers to two directions or two lines having an offset angle of 900 or more therebetween.

The term "substantially aligned" or "substantial alignment" as used herein refers to two directions or two lines having an offset angle of less than 90° therebetween.

The term "primary heat source" as used herein refers to a heat source that provides more than 50%, preferably more than 60%, more preferably more than 70%, most preferably more than 80%, of the total thermal energy absorbed by an object (e.g., the sheet of aerated wet pre-mixture according to the present disclosure).

The term "controlled surface temperature" as used herein refers to a surface temperature that is relatively consistent, i.e., with less than +/−20% fluctuations, preferably less than +/−10% fluctuations, more preferably less than +/−5% fluctuations.

II. Formulations of Solid Sheets

The flexible, porous, dissolvable solid sheet article of the present disclosure comprises at least a water-soluble polymer, a surfactant, and a plurality of microcapsules. It may optionally comprise other adjunct ingredients. In comparison with prior art Post-Added PMCs or other microcapsules, which stay only on one or both planar surfaces of the sheet article to which they are added, Direct-Added PMCs or other microcapsules of the present disclosure are located inside the flexible, porous, dissolvable solid sheet article and between the two opposing planar surfaces of such solid sheet article.

Figure 1B:
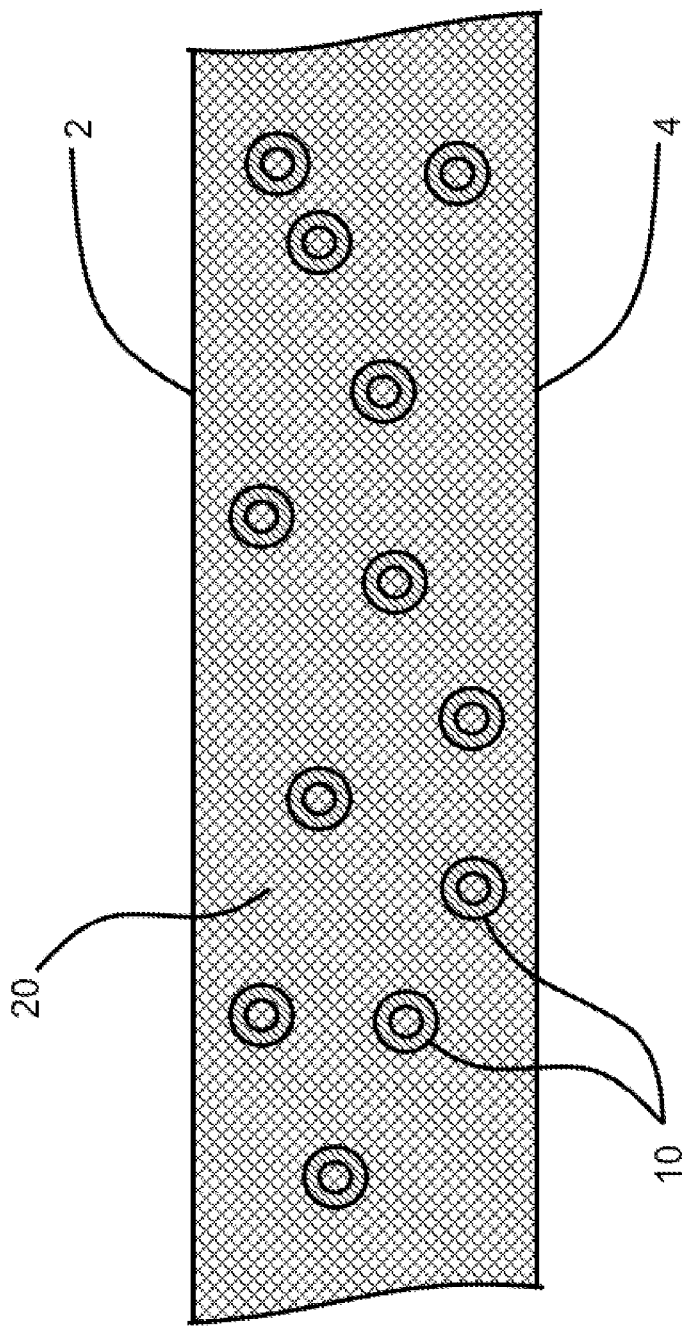
FIG. 1B is a cross-section view of the solid sheet article of FIG. 1A along lines A-A.

To better illustrate this, FIGS. 1A and 1B show schematic and cross-section views of an exemplary flexible, porous, dissolvable solid sheet article 1, which has opposing first and second planar surfaces 2 and 4. At least one of the microcapsules 10 is located between said opposing first and second surfaces 2 and 4, in a matrix 20 formed by the water-soluble polymer, the surfactant, and optionally other adjunct ingredients (not shown). Preferably a majority, more preferably more than 80%, still more preferably more than 90%, most preferably more than 90%, of the microcapsules 10 are located between the opposing first and second surfaces 2 and 4.

1. Microcapsules

Figure 2:
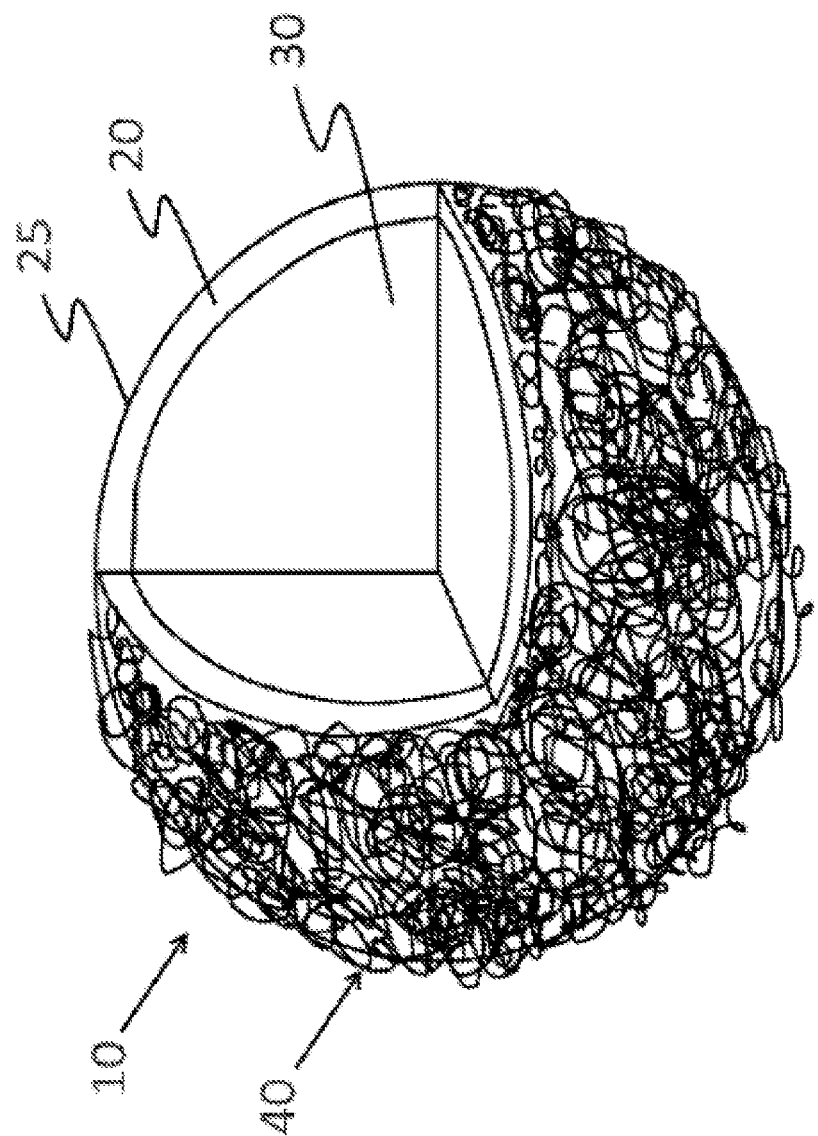
FIG. 2 is a schematic view of a microcapsule according to the present disclosure.

Each of the plurality of microcapsules may include a core and a shell that at least partially surrounds the core. As schematically shown in FIG. 2, a microcapsule 10 may have a core 30 and a shell 20 at least partially surrounding the core 30. The core 30 may include a benefit agent (not shown), such as perfumes. The shell 20 may include an outer surface 25, which may include a coating 40. The coating may be cationic, nonionic or anionic. These elements are discussed in more detail below.

Preferably, the flexible, porous, dissolvable solid sheet article of the present disclosure comprises said plurality of microcapsules in an amount ranging from about 0.1%, or from about 0.2%, or from about 0.5%, or from about 1%, to about 50%, or to about 40%, or to about 30%, or to about 20%, by total weight of said flexible, porous, dissolvable solid sheet article. Preferably, the flexible, porous, dissolvable solid sheet article comprises from about 0.1% to about 50%, more preferably from about 0.2% to about 40%, still more preferably from about 0.5% to about 30%, most preferably from about 1% to about 20%, of microcapsules by total weight of said solid sheet articles.

The core of each of said microcapsules includes a benefit agent that can be selected from the group consisting of perfumes, silicone oils, waxes, hydrocarbons, higher fatty acids, essential oils, lipids, skin coolants, vitamins, sunscreens, antioxidants, glycerin, catalysts, bleach particles, silicone dioxide particles, malodor reducing agents, odor-controlling materials, chelating agents, antistatic agents, softening agents, insect and moth repelling agents, colorants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents, freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, deformers, anti-foaming agents, UV protection agents, sun fade inhibitors, anti-allergic agents, enzymes, water-proofing agents, fabric comfort agents, shrinkage resistance agents, stretch resistance agents, stretch recovery agents, skin care agents, natural actives, antibacterial actives, antiperspirant actives, cationic polymers, dyes and mixtures thereof. Preferably, the benefit agent comprises perfumes.

The shell that at least partially (preferably completely) surround the core may comprise a material selected from the group consisting of polyethylenes, polyamides, polyacrylamides, polystyrenes, polyisoprenes, polycarbonates, polyesters, polyacrylates, polymethacrylates, aminoplasts, polyvinylamines, polyvinyl formamides, polyolefins, polyvinyl alcohols, polysaccharides (e.g., alginate and/or chitosan), gelatin, shellac, epoxy resins, vinyl polymers, water-insoluble inorganics (e.g., silicas), silicones, and combinations thereof. Among these materials, the most stable are polyoxymethyleneurea (PMU)-based materials, including but not limited to urea-formaldehyde and/or melamine-formaldehyde.

In one aspect, the shell comprises an aminoplast polymer selected from the group consisting of polyureas, polyurethanes, and/or polyureaurethanes. Preferably, the shell comprises an aminoplast copolymer, such as melamine-formaldehyde, cross-linked melamine formaldehyde, urea-formaldehyde, cross-linked urea-formaldehyde, and combinations thereof. More preferably, the shell of each of the microcapsules comprises melamine formaldehyde and/or cross-linked melamine formaldehyde.

In a preferred, but not necessary, aspect of the present disclosure, the shell comprises an anionic polymer selected from the group consisting of poly(meth)acrylates, polyvinyl (meth)acrylates, poly(ethylene-maleic anhydride), and combinations thereof. More preferably, the shell of each of the microcapsules comprises polyacrylates.

Optionally, the shell of each of the microcapsules may have one or more coatings formed thereover. The coating(s) may be cationic, nonionic, and/or anionic, and it may comprise a material selected from the group consisting of poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methylacrylate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl methyl ether/maleic anhydride, poly(vinyl pyrrolidone/methacrylamidopropyl trimethyl ammonium chloride), polyvinyl pyrrolidone/dimethylaminoethyl methacrylate, polyvinyl amines, polyallyl amines and copolymers of polyvinyl amines, polyvinyl formamides, and mixtures thereof. Preferably, said coating(s) comprise a material selected from the group consisting of poly(meth)acrylates, poly(ethylene-maleic anhydride), polyamine, polyvinylpyrrolidone, polyvinylpyrrolidone-ethyl acrylate, polyvinylpyrrolidone-vinyl acrylate, polyvinylpyrrolidone methylacrylate, polyvinylpyrrolidone/vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, carboxymethyl cellulose, carboxymethyl hydroxyethyl cellulose, hydroxyethyl cellulose, polyvinyl methyl ether/maleic anhydride, poly(vinyl pyrrolidone/methacrylamidopropyl trimethyl ammonium chloride), polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof. Most preferably, said coating(s) comprise a material selected from the group consisting of poly(meth) acrylates, poly(ethylene-maleic anhydride), polyamine, polyvinylpyrrolidone, polyvinylpyrrolidone-ethyl acrylate, polyvinylpyrrolidone-vinyl acrylate, polyvinylpyrrolidone methylacrylate, polyvinylpyrrolidone/vinyl acetate, polyvinyl acetate, polysiloxane, poly(propylene maleic anhydride), maleic anhydride derivatives, co-polymers of maleic anhydride derivatives, polyvinyl alcohol, carboxymethyl cellulose, carboxymethyl hydroxyethyl cellulose, hydroxyethyl cellulose, polyvinyl methyl ether/maleic anhydride, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof.

In a preferred embodiment of the present disclosure, the shell of each of the microcapsules has a cationic coating thereover, while said cationic coating is formed by a cationic polymer selected from the group consisting of polyvinylformamides, partially hydroxylated polyvinylformamides, polyvinylamines, polyethyleneimines, ethoxylated polyethyleneimines, cationically modified polysaccharides (e.g., cationically modified starch, cationically modified guar, cationically modified hydroxyl ethyl cellulose, and the like), and combinations thereof.

In another example, the coating that coats the shell of each of the above-mentioned microcapsules comprises a cationic polymer and an anionic polymer.

The microcapsules used in the present disclosure are preferably friable microcapsules, i.e., they have a propensity to rupture or break open when subjected to external pressure or shear force. Friable microcapsules as mentioned herein are activated by external pressure or force to release the benefit agent encapsulated in the core, so they are distinguished from moisture-activated microcapsules such as those formed mostly by cyclodextrin.

The microcapsules of the present disclosure can be formed by a variety of procedures that include, but are not limited to: coating, extrusion, spray-drying, interfacial, in-situ and matrix polymerization.

The microcapsules may have a volume weighted mean particle size ranging from about 5 microns to about 500 microns, preferably from about 8 microns to about 200 microns, more preferably from about 10 microns to about 100 microns, as measured by typical methods known in the art, such as with a Malvern Particle Sizer (commercially available from Malvern Panalytical, Ltd., Malvern, UK).

2. Water-Soluble Polymer

As mentioned hereinabove, the flexible, porous, dissolvable solid sheet of the present disclosure may be formed by a wet pre-mixture that comprises a water-soluble polymer, a surfactant, and a plurality of the microcapsules. Such a water-soluble polymer may function in the resulting solid sheet as a film-former, a structurant as well as a carrier for other active ingredients (e.g., surfactants, emulsifiers, builders, chelants, perfumes, colorants, and the like).

Preferably, the wet pre-mixture may comprise from about 3% to about 20% by weight of the pre-mixture of water-soluble polymer, in one embodiment from about 5% to about 15% by weight of the pre-mixture of water-soluble polymer, in one embodiment from about 7% to about 10% by weight of the pre-mixture of water-soluble polymer.

After drying, it is preferred that the water-soluble polymer is present in the flexible, porous, dissolvable solid sheet of the present disclosure in an amount ranging from about 5% to about 50%, preferably from about 8% to about 40%, more preferably from about 10% to about 30%, most preferably from about 11% to about 25%, by total weight of the solid sheet. In a particularly preferred embodiment of the present disclosure, the total amount of water-soluble polymer(s) present in the flexible, porous, dissolvable solid sheet of the present disclosure is no more than 25% by total weight of such sheet.

Water-soluble polymers suitable for the practice of the present disclosure may be selected those with weight average molecular weights ranging from about 50,000 to about 400,000 Daltons, preferably from about 60,000 to about 300,000 Daltons, more preferably from about 70,000 to about 200,000 Daltons, most preferably from about 80,000 to about 150,000 Daltons. The weight average molecular weight is computed by summing the average molecular weights of each polymer raw material multiplied by their respective relative weight percentages by weight of the total weight of polymers present within the porous solid sheet. The weight average molecular weight of the water-soluble polymer used herein may impact the viscosity of the wet pre-mixture, which may in turn influence the bubble number and size during the aeration step as well as the pore expansion/opening results during the drying step. Further, the weight average molecular weight of the water-soluble polymer may affect the overall film-forming properties of the wet pre-mixture and its compatibility/incompatibility with certain surfactants.

The water-soluble polymers of the present disclosure may include, but are not limited to, synthetic polymers including polyvinyl alcohols, polyvinylpyrrolidones, polyalkylene oxides, polyacrylates, caprolactams, polymethacrylates, polymethylmethacrylates, polyacrylamides, polymethylacrylamides, polydimethylacrylamides, polyethylene glycol monomethacrylates, copolymers of acrylic acid and methyl acrylate, polyurethanes, polycarboxylic acids, polyvinyl acetates, polyesters, polyamides, polyamines, polyethyleneimines, maleic/(acrylate or methacrylate) copolymers, copolymers of methylvinyl ether and of maleic anhydride, copolymers of vinyl acetate and crotonic acid, copolymers of vinylpyrrolidone and of vinyl acetate, copolymers of vinylpyrrolidone and of caprolactam, vinyl pyrollidone/vinyl acetate copolymers, copolymers of anionic, cationic and amphoteric monomers, and combinations thereof.

The water-soluble polymers of the present disclosure may also be selected from naturally sourced polymers including those of plant origin examples of which include karaya gum, tragacanth gum, gum Arabic, acemannan, konjac mannan, acacia gum, gum ghatti, whey protein isolate, and soy protein isolate; seed extracts including guar gum, locust bean gum, quince seed, and psyllium seed; seaweed extracts such as carrageenan, alginates, and agar; fruit extracts (pectins); those of microbial origin including xanthan gum, gellan gum, pullulan, hyaluronic acid, chondroitin sulfate, and dextran; and those of animal origin including casein, gelatin, keratin, keratin hydrolysates, sulfonic keratins, albumin, collagen, glutelin, glucagons, gluten, zein, and shellac.

Modified natural polymers can also be used as water-soluble polymers in the present disclosure. Suitable modified natural polymers include, but are not limited to, cellulose derivatives such as hydroxypropylmethylcellulose, hydroxymethylcellulose, hydroxyethylcellulose, methylcellulose, hydroxypropylcellulose, ethylcellulose, carboxymethylcellulose, cellulose acetate phthalate, nitrocellulose and other cellulose ethers/esters; and guar derivatives such as hydroxypropyl guar.

The water-soluble polymer of the present disclosure may include starch. As used herein, the term "starch" includes both naturally occurring or modified starches. Typical natural sources for starches can include cereals, tubers, roots, legumes and fruits. More specific natural sources can include corn, pea, potato, banana, barley, wheat, rice, sago, amaranth, tapioca, arrowroot, canna, sorghum, and waxy or high amylase varieties thereof. The natural starches can be modified by any modification method known in the art to form modified starches, including physically modified starches, such as sheared starches or thermally-inhibited starches; chemically modified starches, such as those which have been cross-linked, acetylated, and organically esterified, hydroxyethylated, and hydroxypropylated, phosphorylated, and inorganically esterified, cationic, anionic, nonionic, amphoteric and zwitterionic, and succinate and substituted succinate derivatives thereof, conversion products derived from any of the starches, including fluidity or thin-boiling starches prepared by oxidation, enzyme conversion, acid hydrolysis, heat or acid dextrinization, thermal and or sheared products may also be useful herein; and pregelatinized starches which are known in the art.

Preferred water-soluble polymers of the present disclosure include polyvinyl alcohols, polyvinylpyrrolidones, polyalkylene oxides, starch and starch derivatives, pullulan, gelatin, hydroxypropylmethylcelluloses, methycelluloses, and carboxymethycelluloses. More preferred water-soluble polymers of the present disclosure include polyvinyl alcohols, and hydroxypropylmethylcelluloses.

Most preferred water-soluble polymers of the present disclosure are polyvinyl alcohols characterized by a degree of hydrolysis ranging from about 40% to about 100%, preferably from about 50% to about 95%, more preferably from about 65% to about 92%, most preferably from about 70% to about 90%. Commercially available polyvinyl alcohols include those from Celanese Corporation (Texas, USA) under the CELVOL trade name including, but not limited to, CELVOL 523, CELVOL 530, CELVOL 540, CELVOL 518, CELVOL 513, CELVOL 508, CELVOL 504; those from Kuraray Europe GmbH (Frankfurt, Germany) under the Mowiol® and POVAL™ trade names; and PVA 1788 (also referred to as PVA BP17) commercially available from various suppliers including Lubon Vinylon Co. (Nanjing, China); and combinations thereof. In a particularly preferred embodiment of the present disclosure, the flexible, porous, dissolvable solid sheet comprises from about 10% to about 25%, more preferably from about 15% to about 23%, by total weight of such sheet, of a polyvinyl alcohol having a weight average molecular weight ranging from 80,000 to about 150,000 Daltons and a degree of hydrolysis ranging from about 80% to about 90%.

In addition to polyvinyl alcohols as mentioned hereinabove, a single starch or a combination of starches may be used as a filler material in such an amount as to reduce the overall level of water-soluble polymers required, so long as it helps provide the solid sheet with the requisite structure and physical/chemical characteristics as described herein. However, too much starch may comprise the solubility and structural integrity of the sheet. Therefore, in preferred embodiments of the present disclosure, it is desired that the solid sheet comprises no more than 20%, preferably from 0% to 10%, more preferably from 0% to 5%, most preferably from 0% to 1%, by weight of the solid sheet, of starch.

3. Surfactant(s)

In addition to the water-soluble polymer described hereinabove, the solid sheet of the present disclosure comprises at least one surfactant. The surfactant may function as emulsifying agents during the aeration process to create a sufficient amount of stable bubbles for forming the desired OCF structure of the present disclosure. Further, the surfactant may function as active ingredients for delivering a desired cleansing benefit.

In a preferred embodiment of the present disclosure, the solid sheet comprises a surfactant selected from the group consisting of anionic surfactants, nonionic surfactants, cationic surfactants, zwitterionic surfactants, amphoteric surfactants, polymeric surfactants and any combinations thereof. Depending on the desired application of such solid sheet and the desired consumer benefit to be achieved, different surfactants can be selected. One benefit of the present disclosure is that the OCF structures of the solid sheet allow for incorporation of a high surfactant content while still providing fast dissolution. Consequently, highly concentrated cleansing compositions can be formulated into the solid sheets of the present disclosure to provide a new and superior cleansing experience to the consumers.

The surfactant as used herein may include both surfactants from the conventional sense (i.e., those providing a consumer-noticeable lathering effect) and emulsifiers (i.e., those that do not provide any lathering performance but are intended primarily as a process aid in making a stable foam structure). Examples of emulsifiers for use as a surfactant component herein include mono- and di-glycerides, fatty alcohols, polyglycerol esters, propylene glycol esters, sorbitan esters and other emulsifiers known or otherwise commonly used to stabilize air interfaces.

The total amount of the surfactant(s) present in the solid sheet of the present disclosure may range widely from about 5% to about 90%, preferably from about 10% to about 80%, more preferably from about 30% to about 70%, by total weight of the solid sheet. Correspondingly, the wet pre-mixture may comprise from about 1% to about 40% by weight of the wet pre-mixture of surfactant(s), in one embodiment from about 2% to about 35% by weight of the wet pre-mixture of surfactant(s), in one embodiment from about 5% to about 30% by weight of the wet pre-mixture of surfactant(s).

In a preferred embodiment of the present disclosure, the solid sheet of the present disclosure comprises from about 30% to about 90%, preferably from about 40% to about 80%, more preferably from about 50% to about 70%, of one or more surfactants by total weight of the solid sheet. In such cases, the wet pre-mixture may comprise from about 10% to about 40% by weight of the wet pre-mixture of surfactant(s), in one embodiment from about 12% to about 35% by weight of the wet pre-mixture of surfactant(s), in one embodiment from about 15% to about 30% by weight of the wet pre-mixture of surfactant(s).

Non-limiting examples of anionic surfactants suitable for use herein include alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof.

One category of anionic surfactants particularly suitable for practice of the present disclosure include $C_6$-$C_{20}$ linear alkylbenzene sulphonate (LAS) surfactant. LAS surfactants are well known in the art and can be readily obtained by sulfonating commercially available linear alkylbenzenes. Exemplary $C_{10}$-$C_{20}$ linear alkylbenzene sulfonates that can be used in the present disclosure include alkali metal, alkaline earth metal or ammonium salts of $C_{10}$-$C_{20}$ linear alkylbenzene sulfonic acids, and preferably the sodium, potassium, magnesium and/or ammonium salts of $C_{11}$-$C_{18}$ or $C_{11}$-$C_{14}$ linear alkylbenzene sulfonic acids. More preferred are the sodium or potassium salts of $C_{12}$ and/or $C_{14}$ linear alkylbenzene sulfonic acids, and most preferred is the sodium salt of $C_{12}$ and/or $C_{14}$ linear alkylbenzene sulfonic acid, i.e., sodium dodecylbenzene sulfonate or sodium tetradecylbenzene sulfonate.

LAS provides superior cleaning benefit and is especially suitable for use in laundry detergent applications. It has been a surprising and unexpected discovery of the present disclosure that when polyvinyl alcohol having a higher weight average molecular weight (e.g., from about 50,000 to about 400,000 Daltons, preferably from about 60,000 to about 300,000 Daltons, more preferably from about 70,000 to about 200,000 Daltons, most preferably from about 80,000 to about 150,000 Daltons) is used as the film-former and carrier, LAS can be used as a major surfactant, i.e., present in an amount that is more than 50% by weight of the total surfactant content in the solid sheet, without adversely affecting the film-forming performance and stability of the overall composition. Correspondingly, in a particular embodiment of the present disclosure, LAS is used as the major surfactant in the solid sheet. If present, the amount of LAS in the solid sheet of the present disclosure may range from about 10% to about 70%, preferably from about 20% to about 65%, more preferably from about 40% to about 60%, by total weight of the solid sheet.

Another category of anionic surfactants suitable for practice of the present disclosure include sodium trideceth sulfates (STS) having a weight average degree of alkoxylation ranging from about 0.5 to about 5, preferably from about 0.8 to about 4, more preferably from about 1 to about 3, most preferably from about 1.5 to about 2.5. Trideceth is a 13-carbon branched alkoxylated hydrocarbon comprising, in one embodiment, an average of at least 1 methyl branch per molecule. STS used by the present disclosure may be include ST(EOxPOy)S, while EOx refers to repeating ethylene oxide units with a repeating number x ranging from 0 to 5, preferably from 1 to 4, more preferably from 1 to 3, and while POy refers to repeating propylene oxide units with a repeating number y ranging from 0 to 5, preferably from 0 to 4, more preferably from 0 to 2. It is understood that a material such as ST2S with a weight average degree of ethoxylation of about 2, for example, may comprise a significant amount of molecules which have no ethoxylate, 1 mole ethoxylate, 3 mole ethoxylate, and so on, while the distribution of ethoxylation can be broad, narrow or truncated, which still results in an overall weight average degree of ethoxylation of about 2. STS is particularly suitable for personal cleansing applications, and it has been a surprising and unexpected discovery of the present disclosure that when polyvinyl alcohol having a higher weight average molecular weight (e.g., from about 50,000 to about 400,000 Daltons, preferably from about 60,000 to about 300,000 Daltons, more preferably from about 70,000 to about 200,000 Daltons, most preferably from about 80,000 to about 150,000 Daltons) is used as the film-former and carrier, STS can be used as a major surfactant, i.e., present in an amount that is more than 50% by weight of the total surfactant content in the solid sheet, without adversely affecting the film-forming performance and stability of the overall composition. Correspondingly, in a particular embodiment of the present disclosure, STS is used as the major surfactant in the solid sheet. If present, the amount of STS in the solid sheet of the present disclosure may range from about 10% to about 70%, preferably from about 20% to about 65%, more preferably from about 40% to about 60%, by total weight of the solid sheet.

Another category of anionic surfactants suitable for practice of the present disclosure include alkyl sulfates. These materials have the respective formulae $ROSO_3M$, wherein R is alkyl or alkenyl of from about 6 to about 20 carbon atoms, x is 1 to 10, and M is a water-soluble cation such as ammonium, sodium, potassium and triethanolamine. Preferably, R has from about 6 to about 18, preferably from about 8 to about 16, more preferably from about 10 to about 14, carbon atoms. Previously, unalkoxylated $C_6$-$C_{20}$ linear or branched alkyl sulfates (AS) have been considered the preferred surfactants in dissolvable solid sheets, especially as the major surfactant therein, due to its compatibility with low molecular weight polyvinyl alcohols (e.g., those with a weight average molecular weight of no more than 50,000 Daltons) in film-forming performance and storage stability. However, it has been a surprising and unexpected discovery of the present disclosure that when polyvinyl alcohol having a higher weight average molecular weight (e.g., from about 50,000 to about 400,000 Daltons, preferably from about 60,000 to about 300,000 Daltons, more preferably from about 70,000 to about 200,000 Daltons, most preferably from about 80,000 to about 150,000 Daltons) is used as the film-former and carrier, other surfactants, such as LAS and/or STS, can be used as the major surfactant in the solid sheet, without adversely affecting the film-forming performance and stability of the overall composition. Therefore, in a particularly preferred embodiment of the present disclosure, it is desirable to provide a solid sheet with no more than about 20%, preferably from 0% to about 10%, more preferably from 0% to about 5%, most preferably from 0% to about 1%, by weight of the solid sheet, of AS.

Another category of anionic surfactants suitable for practice of the present disclosure include $C_6$-$C_{20}$ linear or branched alkylalkoxy sulfates (AAS). Among this category, linear or branched alkylethoxy sulfates (AES) having the respective formulae $RO(C_2H_4O)_xSO_3M$ are particularly preferred, wherein R is alkyl or alkenyl of from about 6 to about 20 carbon atoms, x is 1 to 10, and M is a water-soluble cation such as ammonium, sodium, potassium and triethanolamine. Preferably, R has from about 6 to about 18, preferably from about 8 to about 16, more preferably from about 10 to about 14, carbon atoms. The AES surfactants are typically made as condensation products of ethylene oxide and monohydric alcohol's having from about 6 to about 20 carbon atoms. Useful alcohols can be derived from fats, e.g., coconut oil or tallow, or can be synthetic. Lauryl alcohol and straight chain alcohol's derived from coconut oil are preferred herein. Such alcohol's are reacted with about 1 to about 10, preferably from about 3 to about 5, and especially about 3, molar proportions of ethylene oxide and the resulting mixture of molecular species having, for example, an average of 3 moles of ethylene oxide per mole of alcohol, is sulfated and neutralized. Highly preferred AES are those comprising a mixture of individual compounds, the mixture having an average alkyl chain length of from about 10 to about 16 carbon atoms and an average degree of ethoxylation of from about 1 to about 4 moles of ethylene oxide. If present, the the amount of AAS in the solid sheet of the present disclosure may range from about 2% to about 40%, preferably from about 5% to about 30%, more preferably from about 8% to about 12%, by total weight of the solid sheet.

Other suitable anionic surfactants include water-soluble salts of the organic, sulfuric acid reaction products of the general formula $[R_1—SO_3-M]$, wherein $R^1$ is chosen from the group consisting of a straight or branched chain, saturated aliphatic hydrocarbon radical having from about 6 to about 20, preferably about 10 to about 18, carbon atoms; and M is a cation. Preferred are alkali metal and ammonium sulfonated $C_{10-18}$ n-paraffins. Other suitable anionic surfactants include olefin sulfonates having about 12 to about 24 carbon atoms. The α-olefins from which the olefin sulfonates are derived are mono-olefins having about 12 to about 24 carbon atoms, preferably about 14 to about 16 carbon atoms. Preferably, they are straight chain olefins.

Another class of anionic surfactants suitable for use in the fabric and home care compositions is the β-alkyloxy alkane sulfonates. These compounds have the following formula:

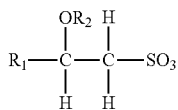

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

Additional examples of suitable anionic surfactants are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Still other suitable anionic surfactants are the succinamates, examples of which include disodium N-octadecylsulfosuccinamate; diammoniumlauryl sulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; and dioctyl esters of sodium sulfosuccinic acid.

Nonionic surfactants that can be included into the solid sheet of the present disclosure may be any conventional nonionic surfactants, including but not limited to: alkyl alkoxylated alcohols, alkyl alkoxylated phenols, alkyl polysaccharides (especially alkyl glucosides and alkyl polyglucosides), polyhydroxy fatty acid amides, alkoxylated fatty acid esters, sucrose esters, sorbitan esters and alkoxylated derivatives of sorbitan esters, amine oxides, and the like. Preferred nonionic surfactants are those of the formula $R^1(OC_2H_4)_nOH$, wherein $R^1$ is a $C_8$-$C_{18}$ alkyl group or alkyl phenyl group, and n is from about 1 to about 80. Particularly preferred are $C_8$-$C_{18}$ alkyl ethoxylated alcohols having a weight average degree of ethoxylation from about 1 to about 20, preferably from about 5 to about 15, more preferably from about 7 to about 10, such as NEODOL® nonionic surfactants commercially available from Shell. Other non-limiting examples of nonionic surfactants useful herein include: $C_6$-$C_{12}$ alkyl phenol alkoxylates where the alkoxylate units may be ethyleneoxy units, propyleneoxy units, or a mixture thereof, $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols (BA); $C_{14}$-$C_{22}$ mid-chain branched alkyl alkoxylates, $BAE_x$, wherein x is from 1 to 30; alkyl polysaccharides, specifically alkyl polyglycosides; Polyhydroxy fatty acid amides; and ether capped poly(oxyalkylated) alcohol surfactants. Suitable nonionic surfactants also include those sold under the tradename Lutensol® from BASF.

In a preferred embodiment, the nonionic surfactant is selected from sorbitan esters and alkoxylated derivatives of sorbitan esters including sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), sorbitan trioleate (SPAN® 85), sorbitan isostearate, polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan monooleate (Tween® 80), polyoxyethylene (4) sorbitan monolaurate (Tween® 21), polyoxyethylene (4) sorbitan monostearate (Tween® 61), polyoxyethylene (5) sorbitan monooleate (Tween® 81), all available from Uniqema, and combinations thereof.

The most preferred nonionic surfactants for practice of the present disclosure include $C_6$-$C_{20}$ linear or branched alkyl-alkoxylated alcohols (AA) having a weight average degree of alkoxylation ranging from 5 to 15, more preferably $C_{12}$-$C_{14}$ linear ethoxylated alcohols having a weight average degree of alkoxylation ranging from 7 to 9. If present, the amount of AA-type nonionic surfactant(s) in the solid sheet of the present disclosure may range from about 2% to about 40%, preferably from about 5% to about 30%, more preferably from about 8% to about 12%, by total weight of the solid sheet.

In a particularly preferred embodiment of the present disclosure, when a majority of the surfactant(s) in the flexible, porous, dissolvable solid sheet article is an anionic and/or nonionic surfactant selected from the group consisting of $C_6$-$C_{20}$ linear alkylbenzene sulfonates (LAS), a $C_6$—$C_{20}$ linear or branched alkylalkoxy sulfates (AAS) having a weight average degree of alkoxylation ranging from 0.5 to 10, $C_6$-$C_{20}$ linear or branched alkyl sulfates (AS), $C_6$-$C_{20}$ linear or branched alkylalkoxylated alcohols (AA) having a weight average degree of alkoxylation ranging from 5 to 15, and combinations thereof, it is preferred that the shell of each of the above-mentioned microcapsules comprises an anionic polymer selected from the group consisting of poly(meth)acrylates, polyvinyl(meth)acrylates, poly(ethylene-maleic anhydride), and combinations thereof. Without being bound by any theory, it is believed that matching the surface charge of the microcapsules with the type of surfactant(s) used in the solid sheet article may further help to reduce the risk of pre-mature rapture/breakage of the microcapsules and to preserve the structural integrity of such microcapsules.

Cationic surfactants can also be utilized in the present disclosure, especially in fabric softener and hair conditioner products. When used in making products that contain cationic surfactants as the major surfactants, it is preferred that such cationic surfactants are present in an amount ranging from about 2% to about 30%, preferably from about 3% to about 20%, more preferably from about 5% to about 15% by total weight of the solid sheet.

For example, the cationic surfactant may be a quaternary ammonium compound and/or an amine compound. Exemplary quaternary ammonium compounds include, but are not limited to, alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof.

Preferred cationic surfactants of the present disclosure include but are not limited to: diester quaternary ammonium (DEQA) compounds, $C_{12}-C_{22}$ mono/di-alkyl quaternary ammonium compounds, $C_{12}-C_{22}$ mono-alkyl amine compounds, and combinations thereof. Yet more particularly, the cationic surfactant may be selected from the group consisting of alkyl trimethyl ammonium compound or amine precursors thereof, dialkyl dimethyl ammonium compound or amine precursors thereof, methyl-diethanolamine-based (MDEA-based) quaternary ammonium compound or amine precursors thereof, methyl-diisopropanolamine-based (MDIPA-based) quaternary ammonium compound or amine precursors thereof, tri-ethanolamine-based (TEA-based) quaternary ammonium compound or amine precursors thereof and any combinations thereof. Most particularly, the cationic surfactant may be selected from the group consisting of behenyl trimethyl ammonium chloride; stearyl trimethyl ammonium chloride; cetyl trimethyl ammonium chloride; lauryl trimethyl ammonium chloride; hydrogenated tallow alkyl trimethyl ammonium chloride, dimethyl hydroxyethyl lauryl ammonium chloride, dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, N,N-di(acyl-oxyethyl)-N,N-dimethylammonium chloride, N,N-di(acyl-oxyisopropyl)-N,N-dimethylammonium methylsulfate, N,N-di(acyl-oxyethyl)-N,N-methylhydroxyethylammonium methylsulfate and any combinations thereof. Exemplary cationic surfactants include diethyl ester dimethyl ammonium chloride (DEEDMAC), dipalmethyl hydroxyethylammoinum methosulfate, coconut trimethyl ammonium chloride and lauryl trimethyl ammonium chloride and the like.

In a particularly preferred embodiment of the present disclosure, the flexible, porous, dissolvable solid sheet article comprises DEQA compounds as a majority surfactant (i.e., being present in an amount that is more than 50% by weight of the total surfactant content in said solid sheet article). DEQA compounds encompass a description of diamido actives as well as actives with mixed amido and ester linkages. Preferred DEQA compounds are typically made by reacting alkanolamines such as MDEA (methyldiethanolamine) and TEA (triethanolamine) with fatty acids. Some materials that typically result from such reactions include N,N-di(acyl-oxyethyl)-N,N-dimethylammonium chloride or N,N-di(acyl-oxyethyl)-N,N-methylhydroxyethylammonium methylsulfate wherein the acyl group is derived from animal fats, unsaturated, and polyunsaturated, fatty acids.

Preferably, the cationic surfactant may comprise DEQA compounds of the following formula:

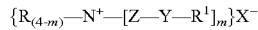

wherein each R comprises either hydrogen, a short chain $C_1-C_6$, in one aspect a $C_1-C_3$ alkyl or hydroxyalkyl group, for example methyl, ethyl, propyl, hydroxyethyl, and the like, poly($C_{2-3}$ alkoxy), polyethoxy, benzyl, or mixtures thereof; each Z is independently $(CH_2)n$, CH2-CH(CH3)- or CH—(CH3)-CH2-; each Y may comprise —O—(O)C—, —C(O)—O—, —NR—C(O)—, or —C(O)—NR—; each m is 2; the sum of carbons in each R1, plus one when Y is —O—(O)C— or —NR—C(O)—, may be $C_{12}-C_{22}$, or $C_{14}-C_{20}$, with each $R^1$ being a hydrocarbyl, or substituted hydrocarbyl group; and $X^-$ may comprise any compatible anion. In one aspect, the compatible anion may comprise chloride, bromide, methylsulfate, ethylsulfate, sulfate, and nitrate. In another aspect, the compatible anion may comprise chloride or methyl sulfate. As used herein, when the diester is specified, it can include the monoester that is present.

A second type of DEQA ("DEQA (2)") compound suitable as an active for use as a cationic surfactant has the general formula:

wherein each Y, R, $R^1$, and $X^-$ have the same meanings as before. An example of a preferred DEQA (2) is the "propyl" ester quaternary ammonium fabric softener active having the formula 1,2-di(acyloxy)-3-trimethylammoniopropane chloride.

In another embodiment, the cationic surfactant comprises one or more softener quaternary ammonium compounds such, but not limited to, as a $C_{12}-C_{22}$ mono-alkyl quaternary ammonium compounds, $C_{12}-C_{22}$ di-alkyl quaternary ammonium compounds, $C_{12}-C_{22}$ mono-alkyl amine compounds, monoester quaternary ammonium compounds, diamido quaternary compounds, and combinations thereof.

Other suitable actives for use as a cationic surfactant include reaction products of fatty acids with dialkylenetriamines in, e.g., a molecular ratio of about 2:1, the reaction products containing compounds of the formula:

wherein $R^1$, $R^2$ are defined as above, and each $R^3$ is a $C_{1-6}$ alkylene group, preferably an ethylene group. Examples of these actives are reaction products of tallow acid, canola acid, or oleic acids with diethylenetriamine in a molecular ratio of about 2:1, the reaction product mixture containing N,N"-ditallowoyldiethylenetriamine, N,N"-dicanola-oyldiethylenetriamine, or N,N"-dioleoyldiethylenetriamine, respectively, with the formula:

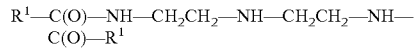

wherein $R^2$ and $R^3$ are divalent ethylene groups, $R^1$ is defined above and an acceptable examples of this structure when $R^1$ is the oleoyl group of a commercially available oleic acid derived from a vegetable or animal source, include EMERSOL® 223LL or EMERSOL® 7021, available from Henkel Corporation.

Another active for use as a cationic surfactant has the formula:

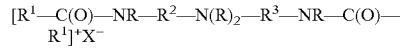

wherein R, $R^1$, $R^2$, $R^3$ and $X^-$ are defined as above. Examples of this active are the di-fatty amidoamines based softener having the formula:

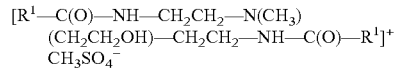

wherein $R^1$—C(O) is an oleoyl group, soft tallow group, or a hardened tallow group available commercially from Degussa under the trade names VARISOFT® 222LT, VARISOFT® 222, and VARISOFT® 110, respectively.

In a particularly preferred embodiment of the present disclosure, when a majority of the surfactant(s) in the flexible, porous, dissolvable solid sheet article is a cationic and/or nonionic surfactant selected from the group consisting of diester quaternary ammonium (DEQA) compounds, $C_{12}-C_{22}$ mono/di-alkyl quaternary ammonium compounds, $C_{12}-C_{22}$ mono-alkyl amine compounds, $C_8-C_{18}$ alkyl ethoxylated alcohols having a weight average degree of ethoxylation from about 1 to about 20, and combinations thereof, it is preferred that each of said microcapsules further comprises a cationic coating over its shell, wherein said cationic coating is formed of a cationic polymer selected from the group consisting of polyvinylformamides, partially hydroxylated polyvinylformamides, polyvinylamines, polyethyleneimines, ethoxylated polyethyleneimines, cationically modified polysaccharides, and combinations thereof. Without being bound by any theory, it is believed that matching the surface charge of the microcapsules with the type of surfactant(s) used in the solid sheet article may further help to reduce the risk of pre-mature rapture/breakage of the microcapsules and to preserve the structural integrity of such microcapsules.

Amphoteric surfactants suitable for use in the solid sheet of the present disclosure includes those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate, and N-higher alkyl aspartic acids.

One category of amphoteric surfactants particularly suitable for incorporation into solid sheets with personal care applications (e.g., shampoo, facial or body cleanser, and the like) include alkylamphoacetates, such as lauroamphoacetate and cocoamphoacetate. Alkylamphoacetates can be comprised of monoacetates and diacetates. In some types of alkylamphoacetates, diacetates are impurities or unintended reaction products. If present, the amount of alkylamphoacetate(s) in the solid sheet of the present disclosure may range from about 2% to about 40%, preferably from about 5% to about 30%, more preferably from about 10% to about 20%, by total weight of the solid sheet.

Zwitterionic surfactants suitable include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Such suitable zwitterionic surfactants can be represented by the formula:

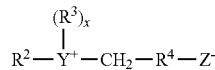

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionic surfactants suitable for use herein include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical, wherein R is a $C_{11}$-$C_{17}$ alkyl, is attached to the nitrogen atom of the betaine are also useful in this invention.

Suitable polymeric surfactants for use in the solid sheet article compositions of the present disclosure include, but are not limited to, block copolymers of ethylene oxide and fatty alkyl residues, block copolymers of ethylene oxide and propylene oxide, hydrophobically modified polyacrylates, hydrophobically modified celluloses, silicone polyethers, silicone copolyol esters, diquaternary polydimethylsiloxanes, and co-modified amino/polyether silicones.

In a preferred embodiment, the surfactant comprises a blend of Group I and Group II surfactants. The blend of surfactants of the present invention comprises one or more surfactants from Group I and one or more surfactants from Group II. Group I surfactants include anionic surfactants, and Group II surfactants include amphoteric surfactants, zwitterionic surfactants, and combinations thereof. In one embodiment of the present invention the ratio of Group I to Group II surfactants is from about 95:5 to about 30:70. In another embodiment of the present invention the ratio of Group I to Group II surfactants is from about 85:15 to about 40:60. In yet another embodiment of the present invention the ratio of Group I to Group II surfactants is from about 70:30 to about 55:45.

Group I Surfactants

The Group I surfactants of the present invention include one or more anionic surfactants. Suitable anionic surfactant components for use in the Dissolvable Article herein include those which are known for use in hair care or other personal care cleansing compositions. The concentration of the anionic surfactant component in the composition should be sufficient to provide the desired cleaning and lather performance, from about 6.5% to about 71% weight % of dry solids of a Group I surfactant.

Anionic surfactants suitable for use in the compositions include alkyl and alkyl ether sulfates. These materials have the respective formulae ROSO3M and RO(C2H4O)xSO3M, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium. Preferably, R has from about 8 to about 18 carbon atoms, more preferably from about 10 to about 16 carbon atoms, even more preferably from about 11 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Synthetic alcohols may include the grades available via Shell Chemical Co. under the NEODOL trade name as NEODOL 91 (C9-11 alcohols), NEODOL 23 (C12-13 alcohols), NEODOL 25 (C12-15 alcohols), NEODOL 45 (C14-15 alcohols), and NEODOL 135 (C11-C13-C15 alcohols). Lauryl alcohol and straight chain alcohols derived from coconut oil or palm kernel oil are preferred. Such alcohols are reacted with between about 0 and about 10, in one embodiment from about 2 to about 5, in another embodiment about 3, molar proportions of ethylene oxide, and the resulting mixture of molecular species having, for example, an average of 3 moles of ethylene oxide per mole of alcohol, is sulfated and neutralized.

Other suitable anionic surfactants are the water-soluble salts of organic, sulfuric acid reaction products conforming to the formula [R1-SO3-M] where R1 is a straight or branched chain, saturated, aliphatic hydrocarbon radical having from about 8 to about 24, preferably about 10 to about 18, carbon atoms; and M is a cation described hereinbefore.

Still other suitable anionic surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278.

Other anionic surfactants suitable for use in the compositions are the succinnates, examples of which include disodium N-octadecylsulfosuccinnate; disodium laurylsulfosuccinate; diammonium laurylsulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic surfactants include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic surfactants suitable for use in the compositions are the beta-alkyloxy alkane sulfonates. These surfactants conform to the formula

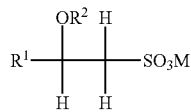

where R1 is a straight chain alkyl group having from about 6 to about 20 carbon atoms, R2 is a lower alkyl group having from about 1 to about 3 carbon atoms, preferably 1 carbon atom, and M is a water-soluble cation as described hereinbefore.

Additional anionic surfactants suitable for use in the compositions include ammonium lauryl sulfate, ammonium laureth sulfate, ammonium laureth-1 sulfate, ammonium laureth-2 sulfate, ammonium laureth-3 sulfate, triethanolamine lauryl sulfate, triethanolamine laureth sulfate, triethanolamine laureth-1 sulfate, triethanolamine laureth-2 sulfate, triethanolamine laureth-3 sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, monoethanolamine lauryl sulfate, sodium tridecyl benzene sulfonate, sodium dodecyl benzene sulfonate, sodium cocoyl isethionate, ammonium decyl sulfate, sodium decyl sulfate, ammonium undecyl sulfate, and ammonium undecyl sulfate and combinations thereof.

In one embodiment of the present invention, one or more of the surfactants is an alkyl sulfate. In one embodiment the one or more alkyl sulfates has an average moles of ethoxylation of from about 0.0 to about 1.9, in another embodiment the one or more alkyl sulfates has an average moles of ethoxylation of from about 0.0 to about 1.5, and in yet another embodiment the one or more alkyl sulfates has an average moles of ethoxylation of from about 0.0 to about 1.0. In one embodiment the one or more alkyl sulfates comprises an ammonium counter ion. Suitable examples of such surfactants with an ammonium counter ion include, but are not limited to, ammonium lauryl sulfate, ammonium laureth-1 sulfate, ammonium laureth-2 sulfate, and combinations thereof.

In one embodiment, one or more Group I surfactants are selected from alkyl sulfates with the following structure:

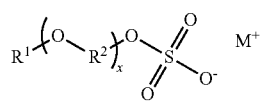

wherein $R^1$ is selected from C-linked monovalent substituents selected from the group consisting of substituted or unsubstituted, straight or branched alkyl or unsaturated alkyl systems comprising an average of 9.0 to 11.9 carbon atoms; $R^2$ is selected from the group consisting of C-linked divalent straight or branched alkyl systems comprising 2 to 3 carbon atoms; $M^+$ is a monovalent counterion selected from sodium, ammonium or protonated triethanolamine; and x is 0.0 to 3.0. In one embodiment, one or more of the alkyl sulfate surfactants according to the above structure comprise an average moles of ethoxylation of from about 0.0 to about 1.9, in another embodiment the alkyl sulfate surfactants according to the above structure comprise an average moles of ethoxylation of from about 0.0 to about 1.5, and in yet another embodiment the alkyl sulfate surfactants according to the above structure comprise an average moles of ethoxylation of from about 0.0 to about 1.0. Suitable examples include ammonium decyl sulfate, sodium decyl sulfate, ammonium undeceyl sulfate, sodium undecyl sulfate, triethanolamine decyl sulfate, or triethanolamine undecyl sulfate. In one embodiment the anionic surfactant of the present invention includes ammonium undecyl sulfate.

Group II Surfactants

The Group II surfactants of the present invention include one or more amphoteric surfactants, zwitterionic surfactants, and/or combinations thereof. Suitable amphoteric or zwitterionic surfactants for use in the composition herein include those which are known for use in hair care or other personal care cleansing. Concentration of such amphoteric surfactants, zwitterionic surfactants and/or combinations thereof, range from about 1.0% to about 52.5% weight % of dry solids. Non limiting examples of suitable zwitterionic or amphoteric surfactants are described in U.S. Pat. No. 5,104,646 (Bolich Jr. et al.), U.S. Pat. No. 5,106,609 (Bolich Jr. et al.).

Amphoteric surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Suitable examples of such amphoteric surfactants include, but are not limited to, sodium cocaminopropionate, sodium cocaminodipropionate, sodium cocoamphoacetate, sodium cocoamphohydroxypropylsulfonate, sodium cocoamphopropionate, sodium cornamphopropionate, sodium lauraminopropionate, sodium lauroamphoacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphohydroxypropylsulfonate, ammonium cocoamphopropionate, ammonium cornamphopropionate, ammonium lauraminopropionate, ammonium lauroamphoacetate, ammonium lauroamphohydroxypropylsulfonate, ammonium lauroamphopropionate, ammonium cornamphopropionate, ammonium lauriminodipropionate, triethanonlamine cocaminopropionate, triethanonlamine cocaminodipropionate, triethanonlamine cocoamphoacetate, triethanonlamine cocoamphohydroxypropylsulfonate, triethanonlamine cocoamphopropionate, triethanonlamine cornamphopropionate, triethanonlamine lauraminopropionate, triethanonlamine lauroamphoacetate, triethanonlamine lauroamphohydroxypropylsulfonate, triethanonlamine lauroamphopropionate, triethanonlamine cornamphopropionate, triethanonlamine lauriminodipropionate, cocoamphodipropionic acid, disodium caproamphodiacetate, disodium caproamphoadipropionate, disodium capryloamphodiacetate, disodium capryloamphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethy-7 carboxyamphodiacetate, lauraminopropionic acid, lauroamphodipropionic acid, lauryl aminopropylglycine, lauryl diethylenediaminoglycine, and combinations thereof.

In one embodiment, the amphoteric surfactant is a surfactant according to the following structure:

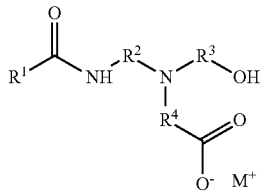

wherein R1 is a C-linked monovalent substituent selected from the group consisting of substituted alkyl systems comprising 9 to 15 carbon atoms, unsubstituted alkyl systems comprising 9 to 15 carbon atoms, straight alkyl systems comprising 9 to 15 carbon atoms, branched alkyl systems comprising 9 to 15 carbon atoms, and unsaturated alkyl systems comprising 9 to 15 carbon atoms; R2, R3, and R4 are each independently selected from the group consisting of C-linked divalent straight alkyl systems comprising 1 to 3 carbon atoms, and C-linked divalent branched alkyl systems comprising 1 to 3 carbon atoms; and M+ is a monovalent counterion selected from the group consisting of sodium, ammonium and protonated triethanolamine. Specific examples of suitable surfactants include sodium cocoamphoacetate, sodium cocoamphodiacetate, sodium lauroamphoacetate, sodium lauroamphodiacetate, ammonium lauroamphoacetate, ammonium cocoamphoacetate, triethanolamine lauroamphoacetate, and triethanolamine cocoamphoacetate.

Zwitterionic surfactants suitable for use in the composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Suitable zwitterionic surfactants include, but are not limited to, cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and combinations thereof.

4. Plasticizers

The flexible, porous, dissolvable solid sheet article of the present disclosure may also comprise a plasticizer, preferably in the amount ranging from about 1% to about 65%, preferably from about 10% to about 60%, more preferably from about 15% to about 55%, yet more preferably from about 20% to about 50%, most preferably from about 22% to about 40%, by total weight of the solid sheet article. Correspondingly, the wet pre-mixture used for forming such solid sheet article may comprise from about 0.1% to about 50%, preferably from about 1% to about 40%, more preferably from about 5% to about 30%, yet more preferably from about 8% to about 25%, most preferably from about 10% to about 20%, of a plasticizer, by weight of the wet pre-mixture.

Suitable plasticizers for use in the present disclosure include, for example, polyols, copolyols, polycarboxylic acids, polyesters, dimethicone copolyols, and the like.

Examples of useful polyols include, but are not limited to: glycerin, diglycerin, ethylene glycol, polyethylene glycol (especially 200-600), propylene glycol, butylene glycol, pentylene glycol, glycerol derivatives (such as propoxylated glycerol), glycidol, cyclohexane dimethanol, hexanediol, 2,2,4-trimethylpentane-1,3-diol, pentaerythritol, urea, sugar alcohols (such as sorbitol, mannitol, lactitol, xylitol, maltitol, and other mono- and polyhydric alcohols), mono-, di- and oligo-saccharides (such as fructose, glucose, sucrose, maltose, lactose, high fructose corn syrup solids, and dextrins), ascorbic acid, sorbates, ethylene bisformamide, amino acids, and the like.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Other suitable platicizers include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

Particularly preferred examples of plasticizers include glycerin, ethylene glycol, polyethylene glycol, propylene glycol, and mixtures thereof. Most preferred plasticizer is glycerin. The presence of a preferred plasticizer, for example glycerin, in the solid sheet may additionally bring about anti-wrinkle benefit. Particularly, when the solid sheet article comprises a preferred amount of glycerin (e.g. from 22% to 40%, by total weight of the solid sheet), the anti-wrinkle effect may be even more significant.

5. Other Ingredients

In addition to the above-described ingredients, e.g., the microcapsules, the water-soluble polymer, the surfactant(s), and the plasticizer, the flexible, porous, dissolvable solid sheet article of the present disclosure may comprise one or more additional ingredients, depending on its intended application. Such one or more additional ingredients may be selected from the group consisting of fabric care actives, dishwashing actives, hard surface cleaning actives, beauty and/or skin care actives, personal cleansing actives, hair care actives, oral care actives, feminine care actives, baby care actives, a bittering agent and any combinations thereof. In a preferred embodiment, the solid sheet of the present disclosure may comprise a bittering agent.

Suitable fabric care actives include but are not limited to: organic solvents (linear or branched lower $C_1$-$C_8$ alcohols, diols, glycerols or glycols; lower amine solvents such as $C_1$-$C_4$ alkanolamines, and mixtures thereof, more specifically 1,2-propanediol, ethanol, glycerol, monoethanolamine and triethanolamine), carriers, hydrotropes, builders, chelants, dispersants, enzymes and enzyme stabilizers, catalytic materials, bleaches (including photobleaches) and bleach activators, perfumes (including encapsulated perfumes or perfume microcapsules), colorants (such as pigments and dyes, including hueing dyes), brighteners, dye transfer inhibiting agents, clay soil removal/anti-redeposition agents, structurants, rheology modifiers, suds suppressors, processing aids, fabric softeners, anti-microbial agents, and the like.

Suitable hair care actives include but are not limited to: moisture control materials of class II for frizz reduction (salicylic acids and derivatives, organic alcohols, and esters), cationic surfactants (especially the water-insoluble type having a solubility in water at 25° C. of preferably below 0.5 g/100 g of water, more preferably below 0.3 g/100 g of water), high melting point fatty compounds (e.g., fatty alcohols, fatty acids, and mixtures thereof with a melting point of 25° C. or higher, preferably 40° C. or higher, more preferably 45° C. or higher, still more preferably 50° C. or higher), silicone compounds, conditioning agents (such as hydrolyzed collagen with tradename Peptein 2000 available from Hormel, vitamin E with tradename Emix-d available from Eisai, panthenol available from Roche, panthenyl ethyl ether available from Roche, hydrolyzed keratin, proteins, plant extracts, and nutrients), preservatives (such as benzyl alcohol, methyl paraben, propyl paraben and imidazolidinyl urea), pH adjusting agents (such as citric acid, sodium citrate, succinic acid, phosphoric acid, sodium hydroxide, sodium carbonate), salts (such as potassium acetate and sodium chloride), coloring agents, perfumes or fragrances, sequestering agents (such as disodium ethylenediamine tetra-acetate), ultraviolet and infrared screening and absorbing agents (such as octyl salicylate), hair bleaching agents, hair perming agents, hair fixatives, anti-dandruff agents, anti-microbial agents, hair growth or restorer agents, co-solvents or other additional solvents, and the like.

Suitable beauty and/or skin care actives include those materials approved for use in cosmetics and that are described in reference books such as the CTFA Cosmetic Ingredient Handbook, Second Edition, The Cosmetic, Toiletries, and Fragrance Association, Inc. 1988, 1992. Further non-limiting examples of suitable beauty and/or skin care actives include preservatives, perfumes or fragrances, coloring agents or dyes, thickeners, moisturizers, emollients, pharmaceutical actives, vitamins or nutrients, sunscreens, deodorants, sensates, plant extracts, nutrients, astringents, cosmetic particles, absorbent particles, fibers, anti-inflammatory agents, skin lightening agents, skin tone agent (which functions to improve the overall skin tone, and may include vitamin B3 compounds, sugar amines, hexamidine compounds, salicylic acid, 1,3-dihydroxy-4-alkybenzene such as hexylresorcinol and retinoids), skin tanning agents, exfoliating agents, humectants, enzymes, antioxidants, free radical scavengers, anti-wrinkle actives, anti-acne agents, acids, bases, minerals, suspending agents, pH modifiers, pigment particles, anti-microbial agents, insect repellents, shaving lotion agents, co-solvents or other additional solvents, and the like.

Suitable bittering agent include a denatonium salt or a derivative thereof. In one aspect, the bittering agent is a denatonium salt selected from the group consisting of denatonium chloride, denatonium citrate, denatonium saccharide, denatonium carbonate, denatonium acetate, denatonium benzoate, and mixtures thereof. In one aspect, the solid sheet comprises a first denatonium salt and the coating composition comprises a second denatonium salt that is different than the first denatonium salt.

A particularly preferred bittering agent is denatonium benzoate, also known as phenylmethyl-[2-[(2,6-dimethylphenyl)amino]-2-oxoethyl]-diethylammonium benzoate, CAS no. 3734-33-6. Denatonium benzoate is commercially sold as BITREX®, available from Macfarlan Smith, Edinburgh, Scotland, UK.

In some aspects, the bittering agent is a natural bitter substance. In some aspects, the bittering agent has a bitter value of from about 1000 to about 200000. In some aspects, the bittering agent is a natural bitter substance with a bitter value of from about 1000 to about 200000, where the natural bitter substance is selected from the group consisting of glycosides, isoprenoids, alkaloids, amino acids, and mixtures thereof. For example, suitable bittering agents also include Quercetin (3,3',4',5,7-pentahydroxyflavone); Naringin (4',5,7-Trihydroxyflavanone-7-rhamnoglucoside); Aucubin; Amarogentin; Dihydrofoliamentin; Gentiopicroside; Gentiopicrin; Swertiamarin; Swerosid; Gentioflavosid;

Centaurosid; Methiafolin; Harpagoside; Centapikrin; Sailicin; Kondurangin; Absinthin; Artabsin; Cnicin; Lactucin; Lactucopicrin; Salonitenolid; a-thujone; β-thujone; Desoxy Limonene; Limonin; Ichangin; iso-Obacunoic Acid; Obacunone; Obacunoic Acid; Nomilin; Ichangin; Nomilinoic acid; Marrubin; Pramarrubin; Carnosol; Carnosic acid; Quassin; Quinine hydrochloride; Quinine sulfate; Quinine dihydrochloride; Columbine; Caffeine; Threonine; Methionine; Phenylalanine; Tryptophan; Arginine; Histidine; Valine; Aspartic acid; Sucrose octaacetate; and mixtures thereof. Other suitable bittering agents include quinine bisulfate and hop extract (e.g., humulone).

The solid sheet article of the present disclosure may comprise from about 0.00001% to about 1%, or about 0.0001% to about 0.5%, or about 0.001% to about 0.25%, or about from about 0.01% to about 0.1%, by weight of the solid sheet, of a bittering agent. In some aspects, the solid sheet article comprises a bittering agent in a sufficient amount to provide a bitter taste.

The solid sheet article of the present disclosure may further comprise other optional ingredients that are known for use or otherwise useful in compositions, provided that such optional materials are compatible with the selected essential materials described herein, or do not otherwise unduly impair product performance.

Non-limiting examples of product type embodiments that can be formed by the solid sheet article of the present disclosure include laundry detergent products, fabric softening products, hand cleansing products, hair shampoo or other hair treatment products, body cleansing products, shaving preparation products, dish cleaning products, personal care substrates containing pharmaceutical or other skin care actives, moisturizing products, sunscreen products, beauty or skin care products, deodorizing products, oral care products, feminine cleansing products, baby care products, fragrance-containing products, and so forth.

III. Processes for Making Solid Sheets

The present disclosure provides a new and improved method for making flexible, porous, dissolvable solid sheets with OCF structures and containing Direct-Added PMCs or other actives-containing microcapsules therein, which comprises the steps of: (a) providing a wet pre-mixture containing raw materials (e.g., the microcapsules, the water-soluble polymer, surfactant(s), and optionally a plasticizer as well as other active ingredients) dissolved or dispersed in water or a suitable solvent, which is characterized by a viscosity of from about 1,000 cps to about 25,000 cps measured at about 40° C. and 1 $s^{-1}$; (b) aerating the wet pre-mixture (e.g., by introducing a gas into the wet slurry) to form an aerated wet pre-mixture characterized by a low density of from about 0.05 to about 0.5 g/ml; (c) forming the aerated wet pre-mixture into a sheet; and (d) drying the formed sheet for a drying time of from 1 minute to 60 minutes at a temperature from 70° C. to 200° C. to form the solid sheet article of the present disclosure. Preferably, the sheet formed by the aerated wet pre-mixture has opposing first and second sides, while the drying of such formed sheet is conducted along a heating direction that forms a temperature gradient decreasing from the first side to the second side of the formed sheet, wherein the heating direction is substantially offset from the gravitational direction for more than half of the drying time, i.e., the drying step is conducted under heating along a mostly "anti-gravity" heating direction. Such a mostly "anti-gravity" heating direction can be achieved by various means, which include but are not limited to the bottom conduction-based heating/drying arrangement and the rotary drum-based heating/drying arrangement.

The processing steps and conditions for forming the flexible, porous, dissolvable solid sheets of the present disclosure, i.e., with OCF structures and containing PMCs and/or other actives-containing microcapsules therein, are described in detail hereinafter.

Step (A): Preparation of Wet Pre-Mixture

The wet pre-mixture of the present disclosure is generally prepared by mixing raw materials of interest, including the microcapsules, the water-soluble polymer, surfactant(s), plasticizer and/or other ingredients, with a sufficient amount of water or another solvent in a pre-mix tank. The wet pre-mixture can be formed using a mechanical mixer. Mechanical mixers useful herein, include, but aren't limited to pitched blade turbines or MAXBLEND mixer (Sumitomo Heavy Industries).

In a preferred but not necessary embodiment of the present disclosure, the microcapsules are provided in a slurry form with a substantial amount of water (e.g., more than 20%, preferably more than 30%, more preferably more than 50%, of water). The microcapsule slurry can be formed by the following processes:

a) preparing a first solution that may comprise, based on total solution weight from 20% to 90%, from 40% to 80%, or even from 60% to 80% water, of a first emulsifier and a first resin, the ratio of said first emulsifier and said first resin being from 0.1:0 to 10:0, from about 0.1:1 to 10:1, from 0.5:1 to 3:1, or even from 0.8:1 to 1.1:1;

b) preparing a second solution that may comprise based on total solution weight from 20% to 95% water, of a second emulsifier and a second resin, the ratio of said second emulsifier and said second resin being from 0:1 to 3:1, from 0.04:1 to 0.2:1, or even from 0.05:1 to 0.15:1;

c) combining a benefit agent (e.g., perfumes) and said first solution to form a first composition;

d) emulsifying said first composition;

e) combining said first composition and said second solution to form a second composition and optionally combining any processing aids and said second composition—said first composition and said second solution may be combined in any order but in one aspect said second solution is added to said first composition or said second solution and said first composition are combined simultaneously;

f) mixing said second composition for at least 15 minutes, at least 1 hour or even from 4 hours to 100 hours at a temperature of from 25° C. to 100° C., from 45° C. to 90° C., or even from 50° C. to 80° C. heat and optionally combining any processing aids to said second composition;

g) optionally combining any scavenger material, structurant, and/or anti-agglomeration agent with said second composition during step f.) or thereafter—such materials may be combined in any order but in one aspect the scavenger material is combined first, any structurant second, and then anti-agglomeration agent is combined; and h) optionally spray drying said second composition.

In one or more aspects of the microcapsule-making process, said first and second resins may comprise the reaction product of an aldehyde and an amine, suitable aldehydes include, formaldehyde. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof.

In one or more aspects of the process, said first and second emulsifiers may comprise a moiety selected from the group consisting of carboxy, hydroxyl, thiol, amine, amide and combinations thereof. In one aspect, said emulsifier may have a pKa of less than 5, preferably greater than 0 but less than 5. Emulsifiers include acrylic acid-alkyl acrylate copolymer, poly(acrylic acid), polyoxyalkylene sorbitan fatty esters, polyalkylene co-carboxy anhydrides, polyalkylene co-maleic anhydrides, poly(methyl vinyl ether-co-maleic anhydride), poly(propylene-co-maleic anhydride), poly(butadiene co-maleic anhydride), and poly(vinyl acetate-co-maleic anhydride), polyvinyl alcohols, polyalkylene glycols, polyoxyalkylene glycols, and mixtures thereof.

In one or more aspects of the process, the pH of the first and second solutions may be controlled such that the pH of said first and second solution is from about 3.0 to 7.0.

In one or more aspects of the process, during step f), from 0% to 10%, from 1% to 5% or even from 2% to 4%, based on total second composition weight, of a salt comprising an anion and cation, said anion being selected from the group consisting of chloride, sulfate, phosphate, nitrate, polyphosphate, citrate, maleate, fumarate and mixtures thereof, and said cation being selected from the group consisting of a Periodic Group IA element, Periodic Group IIA element, ammonium cation and mixtures thereof, preferably sodium sulfate, may be combined with said second composition.

In one or more aspects of the process, any of the aforementioned processing parameters may be combined.

Suitable equipment for use in the processes disclosed herein may include continuous stirred tank reactors, homogenizers, turbine agitators, recirculating pumps, paddle mixers, ploughshear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Kentucky, U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minnesota, U.S.A.), Arde Barinco (New Jersey, U.S.A.).

Such microcapsule-containing slurry is mixed with the other raw materials (e.g., the water-soluble polymer, surfactant(s), plasticizer and/or other ingredients) and a sufficient amount of water or another solvent in a pre-mix tank to form the above-mentioned wet pre-mixture.

It is particularly important in the present disclosure to adjust viscosity of the wet pre-mixture so that it is within a predetermined range of from about 1,000 cps to about 25,000 cps when measured at 40° C. and 1 $s^{-1}$. Viscosity of the wet pre-mixture has a significant impact on the pore expansion and pore opening of the aerated pre-mixture during the subsequent drying step, and wet pre-mixtures with different viscosities may form flexible, porous, dissolvable solid sheets of very different foam structures. On one hand, when the wet pre-mixture is too thick/viscous (e.g., having a viscosity higher than about 25,000 cps as measured at 40° C. and 1 $s^{-1}$), aeration of such wet pre-mixture may become more difficult. More importantly, interstitial liquid drainage from thin film bubble facings into the plateau borders of the three-dimensional foam during the subsequent drying step may be adversely affected or significantly limited. The interstitial liquid drainage during drying is believed to be critical for enabling pore expansion and pore opening in the aerated wet pre-mixture during the subsequent drying step. As a result, the flexible, porous, dissolvable solid sheet so formed thereby may have significantly smaller pores and less interconnectivity between the pores (i.e., more "closed" pores than open pores), which render it harder for water to ingress into and egress from such sheet. On the other hand, when the wet pre-mixture is too thin/running (e.g., having a viscosity lower than about 1,000 cps as measured at 40° C. and 1 $s^{-1}$), the aerated wet pre-mixture may not be sufficiently stable, i.e., the air bubbles may rupture, collapse, or coalescence too quickly in the wet pre-mixture after aeration and before drying. Consequently, the resulting solid sheet may be much less porous and more dense than desired.

In one embodiment, viscosity of the wet pre-mixture ranges from about 3,000 cps to about 24,000 cps, preferably from about 5,000 cps to about 23,000 cps, more preferably from about 10,000 cps to about 20,000 cps, as measured at 40° C. and 1 $sec^{-1}$. The pre-mixture viscosity values are measured using a Malvern Kinexus Lab+ rheometer with cone and plate geometry (CP1/50 SR3468 SS), a gap width of 0.054 mm, a temperature of 40° C. and a shear rate of 1.0 reciprocal seconds for a period of 360 seconds.

In a preferred but not necessary embodiment, the solids of interest are present in the wet pre-mixture at a level of from about 15% to about 70%, preferably from about 20% to about 50%, more preferably from about 25% to about 45% by total weight of the wet pre-mixture. The percent solid content is the summation of the weight percentages by weight of the total processing mixture of all solid components, semi-solid components and liquid components excluding water and any obviously volatile materials such as low boiling alcohols. On one hand, if the solid content in the wet pre-mixture is too high, viscosity of the wet pre-mixture may increase to a level that will prohibit or adversely affect interstitial liquid drainage and prevent formation of the desired predominantly open-celled porous solid structure as described herein. On the other hand, if the solid content in the wet pre-mixture is too low, viscosity of the wet pre-mixture may decrease to a level that will cause bubble rupture/collapse/coalescence and more percent (%) shrinkage of the pore structures during drying, resulting in a solid sheet that is significantly less porous and denser.

Among the solids of interest in the wet pre-mixture of the present disclosure, there may be present from about 0.1% to about 12% microcapsules, 1% to about 75% surfactant(s), from about 0.1% to about 25% water-soluble polymer, and optionally from about 0.1% to about 25% plasticizer, by total weight of the solids. Other actives or benefit agents can also be added into the pre-mixture.

Optionally, the wet pre-mixture is pre-heated immediately prior to and/or during the aeration process at above ambient temperature but below any temperatures that would cause degradation of the components therein. In one embodiment, the wet pre-mixture is kept at an elevated temperature ranging from about 40° C. to about 100° C., preferably from about 50° C. to about 95° C., more preferably from about 60° C. to about 90° C., most preferably from about 75° C. to about 85° C. In one embodiment, the optional continuous heating is utilized before the aeration step. Further, additional heat can be applied during the aeration process to try and maintain the wet pre-mixture at such an elevated temperature. This can be accomplished via conductive heating from one or more surfaces, injection of steam or other processing means. It is believed that the act of pre-heating the wet pre-mixture before and/or during the aeration step may provide a means for lowering the viscosity of pre-mixtures comprising higher percent solids content for improved introduction of bubbles into the mixture and formation of the desired solid sheet. Achieving higher percent solids content is desirable since it may reduce the overall energy requirements for drying. The increase of percent solids may therefore conversely lead to a decrease in water level content and an increase in viscosity. As mentioned hereinabove, wet pre-mixtures with viscosities that are too high are undesirable for the practice of the present disclosure. Pre-heating may effectively counteract such viscosity increase and thus allow for the manufacture of a fast dissolving sheet even when using high solid content pre-mixtures.

Step (B): Aeration of Wet Pre-Mixture

Aeration of the wet pre-mixture is conducted in order to introduce a sufficient amount of air bubbles into the wet pre-mixture for subsequent formation of the OCF structures therein upon drying. Once sufficiently aerated, the wet pre-mixture is characterized by a density that is significantly lower than that of the non-aerated wet pre-mixture (which may contain a few inadvertently trapped air bubbles) or an insufficiently aerated wet pre-mixture (which may contain some bubbles but at a much lower volume percentage and of significantly larger bubble sizes). Preferably, the aerated wet pre-mixture has a density ranging from about 0.05 g/ml to about 0.5 g/ml, preferably from about 0.08 g/ml to about 0.4 g/ml, more preferably from about 0.1 g/ml to about 0.35 g/ml, still more preferably from about 0.15 g/ml to about 0.3 g/ml, most preferably from about 0.2 g/ml to about 0.25 g/ml.

Aeration can be accomplished by either physical or chemical means in the present disclosure. In one embodiment, it can be accomplished by introducing a gas into the wet pre-mixture through mechanical agitation, for example, by using any suitable mechanical processing means, including but not limited to: a rotor stator mixer, a planetary mixer, a pressurized mixer, a non-pressurized mixer, a batch mixer, a continuous mixer, a semi-continuous mixer, a high shear mixer, a low shear mixer, a submerged sparger, or any combinations thereof. In another embodiment, it may be achieved via chemical means, for example, by using chemical foaming agents to provide in-situ gas formation via chemical reaction of one or more ingredients, including formation of carbon dioxide ($CO_2$ gas) by an effervescent system.

In a particularly preferred embodiment, it has been discovered that the aeration of the wet pre-mixture can be cost-effectively achieved by using a continuous pressurized aerator or mixer that is conventionally utilized in the foods industry in the production of marshmallows. Continuous pressurized mixers may work to homogenize or aerate the wet pre-mixture to produce highly uniform and stable foam structures with uniform bubble sizes. The unique design of the high shear rotor/stator mixing head may lead to uniform bubble sizes in the layers of the open celled foam. Suitable continuous pressurized aerators or mixers include the Morton whisk (Morton Machine Co., Motherwell, Scotland), the Oakes continuous automatic mixer (E.T. Oakes Corporation, Hauppauge, New York), the Fedco Continuous Mixer (The Peerless Group, Sidney, Ohio), the Mondo (Haas-Mondomix B.V., Netherlands), the Aeros (Aeros Industrial Equipment Co., Ltd., Guangdong Province, China), and the Preswhip (Hosokawa Micron Group, Osaka, Japan). For example, an Aeros A20 continuous aerator can be operated at a feed pump speed setting of about 300-800 (preferably at about 500-700) with a mixing head speed setting of about 300-800 (preferably at about 400-600) and an air flow rate of about 50-150 (preferably 60-130, more preferably 80-120) respectively. For another example, an Oakes continuous automatic mixer can be operated at a mixing head speed setting of about 10-30 rpm (preferably about 15-25 rpm, more preferably about 20 rpm) with an air flow rate of about 10-30 Litres per hour (preferably about 15-25 L/hour, more preferably about 19-20 L/hour).

In another specific embodiment, aeration of the wet pre-mixture can be achieved by using the spinning bar that is a part of the rotary drum dryer, more specifically a component of the feeding trough where the wet pre-mixture is stored before it is coated onto the heated outer surface of the drum dryer and dried. The spinning bar is typically used for stirring the wet pre-mixture to preventing phase separation or sedimentation in the feeding trough during the waiting time before it is coated onto the heated rotary drum of the drum dryer. In the present disclosure, it is possible to operate such spinning bar at a rotating speed ranging from about 150 to about 500 rpm, preferably from about 200 to about 400 rpm, more preferably from about 250 to about 350 rpm, to mix the wet pre-mixture at the air interface and provide sufficient mechanical agitation needed for achieving the desired aeration of the wet pre-mixture.

As mentioned hereinabove, the wet pre-mixture can be maintained at an elevated temperature during the aeration process, so as to adjust viscosity of the wet pre-mixture for optimized aeration and controlled draining during drying. For example, when aeration is achieved by using the spinning bar of the rotary drum, the aerated wet pre-mixture in the feeding trough is typically maintained at about 60° C. during initial aeration by the spinning bar (while the rotary drum is stationary), and then heated to about 70° C. when the rotary drum is heated up and starts rotating.

Bubble size of the aerated wet pre-mixture assists in achieving uniform layers in the OCF structures of the resulting solid sheet. In one embodiment, the bubble size of the aerated wet pre-mixture is from about 5 to about 100 microns; and in another embodiment, the bubble size is from about 20 microns to about 80 microns. Uniformity of the bubble sizes causes the resulting solid sheets to have consistent densities.

Step (C): Sheet-Forming

After sufficient aeration, the aerated wet pre-mixture forms one or more sheets with opposing first and second sides. The sheet-forming step can be conducted in any suitable manners, e.g., by extrusion, casting, molding, vacuum-forming, pressing, printing, coating, and the like. More specifically, the aerated wet pre-mixture can be formed into a sheet by: (i) casting it into shallow cavities or trays or specially designed sheet moulds; (ii) extruding it onto a continuous belt or screen of a dryer; (iii) coating it onto the outer surface of a rotary drum dryer. Preferably, the supporting surface upon which the sheet is formed is formed by or coated with materials that are anti-corrosion, non-interacting and/or non-sticking, such as metal (e.g., steel, chromium, and the like), TEFLON®, polycarbonate, NEOPRENE®, HDPE, LDPE, rubber, glass and the like.

Preferably, the formed sheet of aerated wet pre-mixture has a thickness ranging from a thickness ranging from 0.5 mm to 4 mm, preferably from 0.6 mm to 3.5 mm, more preferably from 0.7 mm to 3 mm, still more preferably from 0.8 mm to 2 mm, most preferably from 0.9 mm to 1.5 mm. Controlling the thickness of such formed sheet of aerated wet pre-mixture may be important for ensuring that the resulting solid sheet has the desired OCF structures. If the formed sheet is too thin (e.g., less than 0.5 mm in thickness), many of the air bubbles trapped in the aerated wet pre-mixture will expand during the subsequent drying step to form through-holes that extend through the entire thickness of the resulting solid sheet. Such through-holes, if too many, may significantly compromise both the overall structural integrity and aesthetic appearance of the sheet. If the formed sheet is too thick, not only it will take longer to dry, but also it will result in a solid sheet with greater pore size variations between different regions (e.g., top, middle, and bottom regions) along its thickness, because the longer the drying time, the more imbalance of forces may occur through bubble rupture/collapse/coalescence, liquid drainage, pore expansion, pore opening, water evaporation, and the like. Further, multiple layers of relatively thin sheets can be assembled into three-dimensional structures of greater thickness to deliver the desired cleaning benefits or other benefits, while still providing satisfactory pore structures for fast dissolution as well as ensuring efficient drying within a relatively short drying time.

Step (D): Drying Under Anti-Gravity Heating

During the drying step of the sheet-making process according to the present disclosure, the OCF structures are formed under simultaneous mechanisms of water evaporation, bubble collapse, interstitial liquid drainage from the thin film bubble facings into the plateau borders between the bubbles (which generates openings between the bubbles and forms the open cells), and solidification of the pre-mixture. Various processing conditions may influence these mechanisms, e.g., solid content in the wet pre-mixture, viscosity of the wet pre-mixture, gravity, and the drying temperature, and the need to balance such processing conditions so as to achieve controlled drainage and form the desired OCF structures.

It has been a surprising and unexpected discovery of the present disclosure that the direction of thermal energy employed (i.e., the heating direction) during the drying step may also have a significant impact on the resulting OCF structures, in addition to the above-mentioned processing conditions. For example, if the thermal energy is applied in a non-directional matter (i.e., there is no clear heating direction) during the drying step, or if the heating direction is substantially aligned with the gravitational direction (i.e., with an offset angle of less than 90° in between) during most of the drying step, the resulting flexible, porous, dissolvable solid sheet tends to have a top surface with smaller pore openings and greater pore size variations in different regions along the direction across its thickness. In contrast, when the heating direction is offset from the gravitation direction (i.e., with an offset angle of 90° or more therebetween) during most of the drying step, the resulting solid sheet may have a top surface with larger pore openings and reduced pore size variations in different regions along the direction across the thickness of such sheet. Correspondingly, the latter sheets are more receptive to water flowing through and are therefore more dissolvable than the former sheets. While not being bound by any theory, it is believed that the alignment or misalignment between the heating direction and the gravitational direction during the drying step and the duration thereof may significantly affect the interstitial liquid drainage between the bubbles, and correspondingly impacting the pore expansion and pore opening in the solidifying pre-mixture and resulting in solid sheets with very different OCF structures.

Therefore, a key feature of the present disclosure is the use of an anti-gravity heating direction during the drying step, either through the entire drying time or at least through more than half of the drying time. Without being bound by any theory, it is believed that such anti-gravity heating direction may reduce or counteract excessive interstitial liquid drainage toward the bottom region of the formed sheet during the drying step. Further, because the top surface is dried last, it allows longer time for air bubbles near the top surface of the formed sheet to expand and form pore openings on the top surface (because once the wet matrix is dried, the air bubbles can no longer expand or form surface openings). Consequently, the solid sheet formed by drying with such anti-gravity heating is characterized by improved OCF structures that enables faster dissolution as well as other surprising and unexpected benefits.

In a specific embodiment, the anti-gravity heating direction is provided by a conduction-based heating/drying arrangement. For example, the aerated wet pre-mixture can be casted into a mold to form a sheet with two opposing sides. The mold can then be placed on a hot plate or a heated moving belt or any other suitable heating device with a planar heated surface characterized by a controlled surface temperature of from about 80° C. to about 170° C., preferably from about 90° C. to about 150° C., more preferably from about 100° C. to about 140° C. Thermal energy is transferred from the planar heated surface to the bottom surface of the sheet of aerated wet pre-mixture via conduction, so that solidification of the sheet starts with the bottom region and gradually moves upward to reach the top region last. In order to ensure that the heating direction is primarily anti-gravity (i.e., substantially offset from the gravitational direction) during this process, it is preferred that the heated surface is a primary heat source for the sheet during drying. If there are any other heating sources, the overall heating direction may change accordingly. More preferably, the heated surface is the only heat source for the sheet during drying.

In another specific embodiment, the anti-gravity heating direction is provided by a rotary drum-based heating/drying arrangement, which is also referred to as drum drying or roller drying. Drum drying is one type of contact-drying methods, which is used for drying out liquids from a viscous pre-mixture of raw materials over the outer surface of a heated rotatable drum (also referred to as a roller or cylinder) at relatively low temperatures to form sheet-like articles. It is a continuous drying process particularly suitable for drying large volumes. Because the drying is conducted at relatively low temperatures via contact-heating/drying, it normally has high energy efficiency and does not adversely affect the compositional integrity of the raw materials.

The heated rotatable cylinder used in drum drying is heated internally, e.g., by steam or electricity, and it is rotated by a motorized drive installed on a base bracket at a predetermined rotational speed. The heated rotatable cylinder or drum preferably has an outer diameter ranging from about 0.5 meters to about 10 meters, preferably from about 1 meter to about 5 meters, more preferably from about 1.5 meters to about 2 meters. It may have a controlled surface temperature of from about 80° C. to about 170° C., preferably from about 90° C. to about 150° C., more preferably from about 100° C. to about 140° C. Further, such heated rotatable cylinder is rotating at a speed of from about 0.005 rpm to about 0.25 rpm, preferably from about 0.05 rpm to about 0.2 rpm, more preferably from about 0.1 rpm to about 0.18 rpm.

The heated rotatable cylinder is preferably coated with a non-stick coating on its outer surface. The non-stick coating may be overlying on the outer surface of the heated rotatable drum, or it can be fixed to a medium of the outer surface of the heated rotatable drum. The medium includes, but is not limited to, heat-resisting non-woven fabrics, heat-resisting carbon fiber, heat-resisting metal or non-metallic mesh and the like. The non-stick coating can effectively preserve structural integrity of the sheet-like article from damage during the sheet-forming process.

There is also provided a feeding mechanism on the base bracket for adding the aerated wet pre-mixture of raw materials as described hereinabove onto the heated rotatable drum, thereby forming a thin layer of the viscous pre-mixture onto the outer surface of the heated rotatable drum. Such thin layer of the pre-mixture is therefore dried by the heated rotatable drum via contact-heating/drying. The feeding mechanism includes a feeding trough installed on the base bracket, while the feeding trough has installed thereupon at least one (preferably two) feeding hopper(s), an imaging device for dynamic observation of the feeding, and an adjustment device for adjusting the position and inclination angle of the feeding hopper. By using the adjustment device to adjust the distance between the feeding hopper and the outer surface of the heated rotatable drum, the need for different thicknesses of the formed sheet-like article can be met. The adjustment device can also be used to adjust the feeding hopper to different inclination angles so as to meet the material requirements of speed and quality. The feeding trough may also include a spinning bar for stirring the wet pre-mixture therein to avoid phase separation and sedimentation before the wet pre-mixture is coated onto the outer surface of the heated rotatable cylinder. Such spinning bar, as mentioned hereinbefore, can also be used to aerate the wet pre-mixture as needed.

There may also be a heating shield installed on the base bracket, to prevent rapid heat lost. The heating shield can also effectively save energy needed by the heated rotatable drum, thereby achieving reduced energy consumption and provide cost savings. The heating shield is a modular assembly structure, or integrated structure, and can be freely detached from the base bracket. A suction device is also installed on the heating shield for sucking the hot steam, to avoid any water condensate falling on the sheet-like article that is being formed.

There may also be an optional static scraping mechanism installed on the base bracket, for scraping or scooping up the sheet-like article already formed by the heated rotatable drum. The static scraping mechanism can be installed on the base bracket, or on one side thereof, for transporting the already formed sheet-like article downstream for further processing. The static scraping mechanism can automatically or manually move close and go away from the heated rotatable drum.

The making process of the flexible, porous, dissolvable solid sheet of the present disclosure is as follows. Firstly, the heated rotatable drum with the non-stick coating on the base bracket is driven by the motorized drive. Next, the adjustment device adjusts the feeding mechanism so that the distance between the feeding hopper and the outer surface of the heated rotatable drum reaches a preset value. Meanwhile, the feeding hopper adds the aerated wet pre-mixture containing all or some raw materials for making the flexible, porous, dissolvable solid sheet onto an outer surface of the heated rotatable drum, to form a thin layer of the aerated wet pre-mixture thereon with the desired thickness as described hereinabove in the preceding section. Optionally, the suction device of the heating shield sucks the hot steam generated by the heated rotatable drum. Next, the static scraping mechanism scrapes/scoops up a dried/solidified sheet, which is formed by the thin layer of aerated wet pre-mixture after it is dried by the heated rotatable drum at a relatively low temperature (e.g., 130° C.). The dried/solidified sheet can also be manually or automatically peeled off, without such static scraping mechanism and then rolled up by a roller bar.

The total drying time in the present disclosure depends on the formulations and solid contents in the wet pre-mixture, the drying temperature, the thermal energy influx, and the thickness of the sheet material to be dried. Preferably, the drying time is from about 1 minute to about 60 minutes, preferably from about 2 minutes to about 30 minutes, more preferably from about 2 to about 15 minutes, still more preferably from about 2 to about 10 minutes, most preferably from about 2 to about 5 minutes.

During such drying time, the heating direction is so arranged that it is substantially opposite to the gravitational direction for more than half of the drying time, preferably for more than 55% or 60% of the drying time (e.g., as in the rotary drum-based heating/drying arrangement described hereinabove), more preferably for more than 75% or even 100% of the drying time (e.g., as in the bottom conduction-based heating/drying arrangement described hereinabove). Further, the sheet of aerated wet pre-mixture can be dried under a first heating direction for a first duration and then under a second, opposite heating direction under a second duration, while the first heating direction is substantially opposite to the gravitational direction, and while the first duration is anywhere from 51% to 99% (e.g., from 55%, 60%, 65%, 70% to 80%, 85%, 90% or 95%) of the total drying time. Such change in heating direction can be readily achieved by various other arrangements not illustrated herein, e.g., by an elongated heated belt of a serpentine shape that can rotate along a longitudinal central axis.

IV. Physical Characteristics of Solid Sheets

The flexible, porous, dissolvable solid sheet formed by the above-described processing steps is characterized by improved pore structures that allows easier water ingress into the sheet and faster dissolution of the sheet in water. Such improved pore structures are achieved mainly by adjusting various processing conditions as described hereinabove, and they are relatively independent or less influenced by the chemical formulations or the specific ingredients used for making such sheet.

In general, such solid sheet may be characterized by: (i) a Percent Open Cell Content of from about 80% to 100%, preferably from about 85% to 99%, more preferably from about 90% to 98%, as measured by the Test 3 hereinafter; and (ii) an Overall Average Pore Size of from about 100 μm to about 2000 μm, preferably from about 150 μm to about 1000 μm, more preferably from about 200 μm to about 600 μm, as measured by the Micro-CT method described in Test 2 hereinafter. The Overall Average Pore Size defines the porosity of the OCF structure of the present disclosure. The Percent Open Cell Content defines the interconnectivity between pores in the OCF structure of the present disclosure. Interconnectivity of the OCF structure may also be described by a Star Volume or a Structure Model Index (SMI) as disclosed in WO2010077627 and WO2012138820.

Such solid sheet of the present disclosure has opposing top and bottom surfaces, while its top surface may be characterized by a Surface Average Pore Diameter that is greater than about 100 μm, preferably greater than about 110 μm, preferably greater than about 120 μm, more preferably greater than about 130 μm, most preferably greater than about 150 μm, as measured by the SEM method described in Test 1 hereinafter.

Still further, the solid sheet formed by the improved heating/drying (for example, rotary drum-based heating/ drying) arrangement of the present disclosure is characterized by a more uniform pore size distribution between different regions along its thickness direction, in comparison with the sheets formed by other heating/drying arrangements (for example, impingement oven-based). Specifically, the solid sheet of the present disclosure comprises a top region adjacent to the top surface, a bottom region adjacent to the bottom surface, and a middle region therebetween, while the top, middle, and bottom regions all have the same thickness. Each of the top, middle and bottom regions of such solid sheet is characterized by an Average Pore Size, while the ratio of Average Pore Size in the bottom region over that in the top region (i.e., bottom-to-top Average Pore Size ratio) is from about 0.6 to about 1.5, preferably from about 0.7 to about 1.4, preferably from about 0.8 to about 1.3, more preferably from about 1 to about 1.2. In comparison, a solid sheet formed by an impingement oven-based heating/drying arrangement may have a bottom-to-top Average Pore Size ratio of more than 1.5, typically about 1.7-2.2 (as demonstrated in Example 1 hereinafter). Moreover, the solid sheet of the present disclosure may be characterized by a bottom-to-middle Average Pore Size ratio of from about 0.5 to about 1.5, preferably from about 0.6 to about 1.3, more preferably from about 0.8 to about 1.2, most preferably from about 0.9 to about 1.1, and a middle-to-top Average Pore Size ratio of from about 1 to about 1.5, preferably from about 1 to about 1.4, more preferably from about 1 to about 1.2.

Still further, the relative standard deviation (RSTD) between Average Pore Sizes in the top, middle and bottom regions of the solid sheet of the present disclosure is no more than 20%, preferably no more than 15%, more preferably no more than 10%, most preferably no more than 5%. In contrast, a solid sheet formed by an impingement oven-based heating/drying arrangement may have a relative standard deviation (RSTD) between top/middle/bottom Average Pore Sizes of more than 20%, likely more than 25% or even more than 35%.

Preferably, the solid sheet of the present disclosure is further characterized by an Average Cell Wall Thickness of from about 5 µm to about 200 µm, preferably from about 10 µm to about 100 µm, more preferably from about 10 µm to about 80 µm, as measured by Test 2 hereinafter.

The solid sheet of the present disclosure may contain a small amount of water. Preferably, it is characterized by a final moisture content of from 0.5% to 25%, preferably from 1% to 20%, more preferably from 3% to 10%, by weight of the solid sheet, as measured by Test 4 hereinafter. An appropriate final moisture content in the resulting solid sheet may ensure the desired flexibility/deformability of the sheet, as well as providing soft/smooth sensory feel to the consumers. If the final moisture content is too low, the sheet may be too brittle or rigid. If the final moisture content is too high, the sheet may be too sticky, and its overall structural integrity may be compromised.

The solid sheet of the present disclosure may have a thickness ranging from about 0.6 mm to about 3.5 mm, preferably from about 0.7 mm to about 3 mm, more preferably from about 0.8 mm to about 2 mm, most preferably from about 1 mm to about 2 mm. Thickness of the solid sheet can be measured using Test 5 described hereinafter. The solid sheet after drying may be slightly thicker than the sheet of aerated wet pre-mixture, due to pore expansion that in turn leads to overall volume expansion.

The solid sheet of the present disclosure may further be characterized by a basis weight of from about 50 grams/m$^2$ to about 500 grams/m$^2$, preferably from about 150 grams/m$^2$ to about 450 grams/m$^2$, more preferably from about 250 grams/m$^2$ to about 400 grams/m$^2$, as measured by Test 6 described hereinafter.

Still further, the solid sheet of the present disclosure may have a density ranging from about 0.05 grams/cm$^3$ to about 0.5 grams/cm$^3$, preferably from about 0.06 grams/cm$^3$ to about 0.4 grams/cm$^3$, more preferably from about 0.07 grams/cm$^3$ to about 0.2 grams/cm$^3$, most preferably from about 0.08 grams/cm$^3$ to about 0.15 grams/cm$^3$, as measured by Test 7 hereinafter. Density of the solid sheet of the present disclosure is lower than that of the sheet of aerated wet pre-mixture, also due to pore expansion that in turn leads to overall volume expansion. In some embodiments, the solid sheets of the present disclosure may have a density of from about 0.06 grams/cm$^3$ to about 0.16 grams/cm$^3$, preferably from about 0.07 grams/cm$^3$ to about 0.15 grams/cm$^3$, more preferably from about 0.08 grams/cm$^3$ to about 0.145 grams/cm$^3$. The solid article containing sheets with such relatively low density may achieve even more improved leakage performance.

Furthermore, the solid sheet of the present disclosure can be characterized by a Specific Surface Area of from about 0.03 m$^2$/g to about 0.25 m$^2$/g, preferably from about 0.04 m$^2$/g to about 0.22 m$^2$/g, more preferably from 0.05 m$^2$/g to 0.2 m$^2$/g, most preferably from 0.1 m$^2$/g to 0.18 m$^2$/g, as measured by Test 8 described hereinafter. The Specific Surface Area of the solid sheet of the present disclosure may be indicative of its porosity and may impact its dissolution rate, e.g., the greater the Specific Surface Area, the more porous the sheet and the faster its dissolution rate.

In a preferred embodiment, the solid sheet according to the present disclosure and/or the dissolvable solid article according to the present disclosure is characterized by:
  a Percent Open Cell Content of from 85% to 99%, preferably from 90% to 98%; and/or
  an Overall Average Pore Size of from 150 µm to 1000 µm, preferably from 200 µm to 600 µm; and/or
  an Average Cell Wall Thickness of from 5 µm to 200 µm, preferably from 10 µm to 100 µm, more preferably from 10 µm to 80 µm; and/or
  a final moisture content of from 0.5% to 25%, preferably from 1% to 20%, more preferably from 3% to 10%, by weight of the solid sheet article; and/or
  a thickness of from 0.6 mm to 3.5 mm, preferably from 0.7 mm to 3 mm, more preferably from 0.8 mm to 2 mm, most preferably from 1 mm to 2 mm; and/or
  a basis weight of from about 50 grams/m$^2$ to about 500 grams/m$^2$, preferably from about 150 grams/m$^2$ to about 450 grams/m$^2$, more preferably from about 250 grams/m$^2$ to about 400 grams/m$^2$; and/or
  a density of from 0.05 grams/cm$^3$ to 0.5 grams/cm$^3$, preferably from 0.06 grams/cm$^3$ to 0.4 grams/cm$^3$, more preferably from 0.07 grams/cm$^3$ to 0.2 grams/cm$^3$, most preferably from 0.08 grams/cm$^3$ to 0.15 grams/cm$^3$; and/or
  a Specific Surface Area of from 0.03 m$^2$/g to 0.25 m$^2$/g, preferably from 0.04 m$^2$/g to 0.22 m$^2$/g, more preferably from 0.05 m$^2$/g to 0.2 m$^2$/g, most preferably from 0.1 m$^2$/g to 0.18 m$^2$/g.

V: Conversion

Once the flexible, dissolvable, porous solid sheet of the present disclosure is formed, as described hereinabove, two or more of such sheets can be further combined and/or treated to form dissolvable solid articles of any desirable three-dimensional shapes, including but not limited to:

spherical, cubic, rectangular, oblong, cylindrical, rod, sheet, flower-shaped, fan-shaped, star-shaped, disc-shaped, and the like. The sheets can be combined and/or treated by any means known in the art, examples of which include but are not limited to, chemical means, mechanical means, and combinations thereof. Such combination and/or treatment steps are hereby collectively referred to as a "conversion" process, i.e., which functions to convert two or more flexible, dissolvable, porous sheets of the present disclosure into a dissolvable solid article with a desired three-dimensional shape.

Furthermore, the multilayer dissolvable solid articles of the present disclosure may be characterized by a maximum dimension D and a minimum dimension z (which is perpendicular to the maximum dimension), while the ratio of D/z (hereinafter also referred to as the "Aspect Ratio") ranges from 1 to about 10, preferably from about 1.4 to about 9, preferably from about 1.5 to about 8, more preferably from about 2 to about 7. Note that when the Aspect Ratio is 1, the dissolvable solid article has a spherical shape. When the Aspect Ratio is about 1.4, the dissolvable solid article has a cubical shape. The multilayer dissolvable solid article of the present disclosure may have a minimal dimension z that is greater than about 3 mm but less than about 20 cm, preferably from about 4 mm to about 10 cm, more preferably from about 5 mm to about 30 mm.

The above-described multilayer dissolvable solid article may comprise more than two of such flexible, dissolvable, porous sheets. For example, it may comprise from about 4 to about 50, preferably from about 5 to about 40, more preferably from about 6 to about 30, of the flexible, dissolvable, porous sheets. The improved OCF structures in the flexible, dissolvable, porous sheets made according to the present disclosure allow stacking of many sheets (e.g., 15-40) together, while still providing a satisfactory overall dissolution rate for the stack.

In a particularly preferred embodiment of the present disclosure, the multilayer dissolvable solid article comprises from 15 to 40 layers of the above-described flexible, dissolvable, porous sheets and has an aspect ratio ranging from about 2 to about 7.

The multilayer dissolvable solid article of the present disclosure may comprise individual sheets of different colors, which are visual from an external surface (e.g., one or more side surfaces) of such article. Such visible sheets of different colors are aesthetically pleasing to the consumers. Further, the different colors of individual sheets may provide visual cues indicative of different benefit agents contained in the individual sheets. For example, the multilayer dissolvable solid article may comprise a first sheet that has a first color and contains a first benefit agent and a second sheet that has a second color and contains a second benefit, while the first color provides a visual cue indicative of the first benefit agent, and while the second color provides a visual cue indicative of the second benefit agent.

Further, one or more functional ingredients can be "sandwiched" between individual sheets of the multilayer dissolvable solid article as described hereinabove, e.g., by spraying, sprinkling, dusting, coating, spreading, dipping, injecting, or even vapor deposition. In order to avoid interference of such functional ingredients with the cutting seal or edge seal near the peripherals of the individual sheets, it is preferred that such functional ingredients are located within a central region between two adjacent sheets, which is defined as a region that is spaced apart from the peripherals of such adjacent sheets by a distance that is at least 10% of the maximum Dimension D. Suitable functional ingredients can be selected from the group consisting of cleaning actives (surfactants, free perfumes, encapsulated perfumes, perfume microcapsules, silicones, softening agents, enzymes, bleaches, colorants, builders, rheology modifiers, pH modifiers, and combinations thereof) and personal care actives (e.g., emollients, humectants, conditioning agents, and combinations thereof).

In a particularly preferred embodiment of the present disclosure, a coating composition is applied on at least one surface of at least one of the above-mentioned two or more flexible, dissolvable, porous sheets before said two or more sheets are stacked together to form the three-dimensional multilayer shape. The coating composition may be applied between individual sheets of the multilayer dissolvable solid article by any appropriate means, e.g., by spraying, sprinkling, dusting, coating, spreading, dipping, injecting, rolling, or even vapor deposition. The coating composition may comprise surfactant(s), perfume(s), a solvent (e.g., glycerol, diethylene glycol, dipropylene glycol, ethanol, water, and the like), a rheology modifier (e.g., cellulose; guar; polyethylene oxide, polypropylene oxide, and POE-PPO copolymers; polyvinylpyrrolidone, crosslinked polyvinylpyrrolidone; polyvinylalcohol; polyethyleneimine; silicon dioxide; water-swellable clays; gums; and derivatives thereof), and/or other ingredients. Said coating composition is characterized by a a viscosity of from about 1 cps to about 25,000 cps, preferably from about 2 cps to about 10,000 cps, more preferably from about 3 cps to about 5,000 cps, most preferably from about 1,000 cps to about 5,000 cps, as measured at about 20° C. and 1 s$^{-1}$. The viscosity of the coating composition can be measured using a Malvern Kinexus Lab+ rheometer with cone and plate geometry (CP1/50 SR3468 SS), a gap width of 0.054 mm, a temperature of 20° C. and a shear rate of 1.0 reciprocal seconds for a period of 360 seconds.

Preferably, the two or more sheets are stacked together so that the coating composition is not present on any of the outer surfaces of the stack. It has been a surprising and unexpected discovery of the present disclosure that three-dimensional multilayer solid articles containing the coating composition have significantly improved dissolution profiles than multilayer solid articles having the same overall amount of surfactants but without the coating composition.

Test Methods

Test 1: Scanning Electron Microscopic (SEM) Method for Determining Surface Average Pore Diameter of the Sheet Article A Hitachi TM3000 Tabletop Microscope (S/N: 123104-04) is used to acquire SEM micrographs of samples. Samples of the solid sheet articles of the present disclosure are approximately 1 cm×1 cm in area and cut from larger sheets. Images are collected at a magnification of 50×, and the unit is operated at 15 kV. A minimum of 5 micrograph images are collected from randomly chosen locations across each sample, resulting in a total analyzed area of approximately 43.0 mm$^2$ across which the average pore diameter is estimated.

The SEM micrographs are then firstly processed using the image analysis toolbox in Matlab. Where required, the images are converted to grayscale. For a given image, a histogram of the intensity values of every single pixel is generated using the 'imhist' Matlab function. Typically, from such a histogram, two separate distributions are obvious, corresponding to pixels of the brighter sheet surface and pixels of the darker regions within the pores. A threshold value is chosen, corresponding to an intensity value between the peak value of these two distributions. All pixels having an intensity value lower than this threshold value are then set to an intensity value of 0, while pixels having an intensity value higher are set to 1, thus producing a binary black and white image. The binary image is then analyzed using ImageJ (https://imagej.nih.gov, version 1.52a), to examine both the pore area fraction and pore size distribution. The scale bar of each image is used to provide a pixel/mm scaling factor. For the analysis, the automatic thresholding and the analyze particles functions are used to isolate each pore. Output from the analyze function includes the area fraction for the overall image and the pore area and pore perimeter for each individual pore detected.

Average Pore Diameter is defined as $D_A50$: 50% of the total pore area is comprised of pores having equal or smaller hydraulic diameters than the $D_A50$ average diameter.

$$\text{Hydraulic diameter}='4*\text{Pore area (m}^2)/\text{Pore perimeter (m)}'.$$

It is an equivalent diameter calculated to account for the pores not all being circular.

Test 2: Micro-Computed Tomographic (µCT) Method for Determining Overall or Regional Average Pore Size and Average Cell Wall Thickness of the Open Cell Foams (OCF)

Porosity is the ratio between void-space to the total space occupied by the OCF. Porosity can be calculated from µCT scans by segmenting the void space via thresholding and determining the ratio of void voxels to total voxels. Similarly, solid volume fraction (SVF) is the ratio between solid-space to the total space, and SVF can be calculated as the ratio of occupied voxels to total voxels. Both Porosity and SVF are average scalar-values that do not provide structural information, such as, pore size distribution in the height-direction of the OCF, or the average cell wall thickness of OCF struts.

To characterize the 3D structure of the OCFs, samples are imaged using a pCT X-ray scanning instrument capable of acquiring a dataset at high isotropic spatial resolution. One example of suitable instrumentation is the SCANCO system model 50 µCT scanner (Scanco Medical AG, Brüttisellen, Switzerland) operated with the following settings: energy level of 45 kVp at 133 µA; 3000 projections; 15 mm field of view; 750 ms integration time; an averaging of 5; and a voxel size of 3 µm per pixel. After scanning and subsequent data reconstruction is complete, the scanner system creates a 16 bit data set, referred to as an ISQ file, where grey levels reflect changes in x-ray attenuation, which in turn relates to material density. The ISQ file is then converted to 8 bit using a scaling factor.

Scanned OCF samples are normally prepared by punching a core of approximately 14 mm in diameter. The OCF punch is laid flat on a low-attenuating foam and then mounted in a 15 mm diameter plastic cylindrical tube for scanning. Scans of the samples are acquired such that the entire volume of all the mounted cut sample is included in the dataset. From this larger dataset, a smaller sub-volume of the sample dataset is extracted from the total cross section of the scanned OCF, creating a 3D slab of data, where pores can be qualitatively assessed without edge/boundary effects.

To characterize pore-size distribution in the height-direction, and the strut-size, Local Thickness Map algorithm, or LTM, is implemented on the subvolume dataset. The LTM Method starts with a Euclidean Distance Mapping (EDM) which assigns grey level values equal to the distance each void voxel is from its nearest boundary. Based on the EDM data, the 3D void space representing pores (or the 3D solid space representing struts) is tessellated with spheres sized to match the EDM values. Voxels enclosed by the spheres are assigned the radius value of the largest sphere. In other words, each void voxel (or solid voxel for struts) is assigned the radial value of the largest sphere that that both fits within the void space boundary (or solid space boundary for struts) and includes the assigned voxel.

The 3D labelled sphere distribution output from the LTM data scan can be treated as a stack of two dimensional images in the height-direction (or Z-direction) and used to estimate the change in sphere diameter from slice to slice as a function of OCF depth. The strut thickness is treated as a 3D dataset and an average value can be assessed for the whole or parts of the subvolume. The calculations and measurements were done using AVIZO Lite (9.2.0) from Thermo Fisher Scientific and MATLAB (R2017a) from Mathworks.

Test 3: Percent Open Cell Content of the Sheet Article

The Percent Open Cell Content is measured via gas pycnometry. Gas pycnometry is a common analytical technique that uses a gas displacement method to measure volume accurately. Inert gases, such as helium or nitrogen, are used as the displacement medium. A sample of the solid sheet article of the present disclosure is sealed in the instrument compartment of known volume, the appropriate inert gas is admitted, and then expanded into another precision internal volume. The pressure before and after expansion is measured and used to compute the sample article volume.

ASTM Standard Test Method D2856 provides a procedure for determining the percentage of open cells using an older model of an air comparison pycnometer. This device is no longer manufactured. However, one can determine the percentage of open cells conveniently and with precision by performing a test which uses Micromeritics' AccuPyc Pycnometer. The ASTM procedure D2856 describes 5 methods (A, B, C, D, and E) for determining the percent of open cells of foam materials. For these experiments, the samples can be analyzed using an Accupyc 1340 using nitrogen gas with the ASTM foampyc software. Method C of the ASTM procedure is to be used to calculate to percent open cells. This method simply compares the geometric volume as determined using calipers and standard volume calculations to the open cell volume as measured by the Accupyc, according to the following equation:

$$\text{Open cell percentage} = \text{Open cell volume of sample}/\text{Geometric volume of sample}*100$$

It is recommended that these measurements be conducted by Micromeretics Analytical Services, Inc. (One Micromeritics Dr, Suite 200, Norcross, GA 30093). More information on this technique is available on the Micromeretics Analytical Services web sites (www.particletesting.com or www.micromeritics.com), or published in "Analytical Methods in Fine particle Technology" by Clyde Orr and Paul Webb.

Test 4: Final Moisture Content of the Sheet Article

Final moisture content of the solid sheet article of the present disclosure is obtained by using a Mettler Toledo HX204 Moisture Analyzer (S/N B706673091). A minimum of 1 g of the dried sheet article is placed on the measuring tray. The standard program is then executed, with additional program settings of 10 minutes analysis time and a temperature of 110° C.

Test 5: Thickness of the Sheet Article

Thickness of the flexible, porous, dissolvable solid sheet article of the present disclosure is obtained by using a micrometer or thickness gage, such as the Mitutoyo Corporation Digital Disk Stand Micrometer Model Number IDS-1012E (Mitutoyo Corporation, 965 Corporate Blvd, Aurora, IL, USA 60504). The micrometer has a 1-inch diameter platen weighing about 32 grams, which measures thickness at an application pressure of about 0.09 psi (6.32 μm/cm$^2$).

The thickness of the flexible, porous, dissolvable solid sheet article is measured by raising the platen, placing a section of the sheet article on the stand beneath the platen, carefully lowering the platen to contact the sheet article, releasing the platen, and measuring the thickness of the sheet article in millimeters on the digital readout. The sheet article should be fully extended to all edges of the platen to make sure thickness is measured at the lowest possible surface pressure, except for the case of more rigid substrates which are not flat.

Test 6: Basis Weight of the Sheet Article

Basis Weight of the flexible, porous, dissolvable solid sheet article of the present disclosure is calculated as the weight of the sheet article per area thereof (grams/m$^2$). The area is calculated as the projected area onto a flat surface perpendicular to the outer edges of the sheet article. The solid sheet articles of the present disclosure are cut into sample squares of 10 cm×10 cm, so the area is known. Each of such sample squares is then weighed, and the resulting weight is then divided by the known area of 100 cm$^2$ to determine the corresponding basis weight.

For an article of an irregular shape, if it is a flat object, the area is thus computed based on the area enclosed within the outer perimeter of such object. For a spherical object, the area is thus computed based on the average diameter as $3.14 \times (\text{diameter}/2)^2$. For a cylindrical object, the area is thus computed based on the average diameter and average length as diameter×length. For an irregularly shaped three-dimensional object, the area is computed based on the side with the largest outer dimensions projected onto a flat surface oriented perpendicularly to this side. This can be accomplished by carefully tracing the outer dimensions of the object onto a piece of graph paper with a pencil and then computing the area by approximate counting of the squares and multiplying by the known area of the squares or by taking a picture of the traced area (shaded-in for contrast) including a scale and using image analysis techniques.

Test 7: Density of the Sheet Article

Density of the flexible, porous, dissolvable solid sheet article of the present disclosure is determined by the equation: Calculated Density=Basis Weight of porous solid/(Porous Solid Thickness×1,000). The Basis Weight and Thickness of the dissolvable porous solid are determined in accordance with the methodologies described hereinabove.

Test 8: Specific Surface Area of the Sheet Article

The Specific Surface Area of the flexible, porous, dissolvable solid sheet article is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the combined weight of the degassed sample and the sample tube. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved. Samples may then analyzed using an ASAP 2420 with krypton gas adsorption. It is recommended that these measurements be conducted by Micromeretics Analytical Services, Inc. (One Micromeritics Dr, Suite 200, Norcross, GA 30093). More information on this technique is available on the Micromeretics Analytical Services web sites (www.particletesting.com or www.micromeritics.com), or published in a book, "Analytical Methods in Fine Particle Technology", by Clyde Orr and Paul Webb.

Test 9: Hand Dissolution Method

One sample article, with dimensions of approximately 30 mm×30 mm×3-5 mm, is placed in the palm of the tester's hand while wearing nitrile gloves. Tap water of about 10 cm$^3$ with a temperature of from about 20° C. to 25° C. is quickly applied to the sample article via a syringe. Using a circular motion, palms of the tester's hands are rubbed together for 2 strokes at a time until dissolution occurs (up to 30 strokes). The hand dissolution speed is reported as the number of strokes (with the upper limit of 30 strokes) that it takes for the sample article to completely dissolve. The higher the number of strokes, the slower the hand dissolution speed. The lower the number of strokers, the faster the hand dissolution speed.

Test 10: Long-Lasting Freshness Test

A basin is filled with 13 liters of reverse osmosis ("RO") water with a temperature of about 28° C. The sample article is immersed in such water for 5 seconds for it to dissolve and form a washing liquor. The washing liquor is agitated by hand for 30 seconds to ensure complete dissolution of the sample article. Test fabrics (containing 0.2 kg of hand towels) are placed into the washing liquor and soaked for 5 minutes. The test fabrics are then removed from the washing liquor and wrung by hand to remove excess water. Subsequently, the test fabrics are hung up and dried overnight. The dried fabrics are subjected to sniff tests by a sensory panel of 4 trained panelists. Each panelist will sniff the dried fabrics before and after rubbing and provide his/her assessments accordingly. The individual assessments are then averaged to provide an overall long-lasting freshness score.

EXAMPLES

Example 1: Comparative Dissolution Profiles of Solid Sheet Articles Containing Direct-Added PMCs and Those Containing Post-Added PMCs 1) Preparation of Solid Sheet Articles with Direct-Added PMCs Flexible, porous and dissolvable solid sheet articles containing the Direct-Added PMCs are prepared as follows.

First, a wet pre-mixture containing 2.44% of a PMC slurry (containing 32.25% PMCs and 67.75% water), 9.61% of PVA, 9.86% of DEEDMAC, 13.44% of glycerin, 1.29% of starch, and a balance of water to result in a total solids content of about 35% by weight (i.e., the total water content in the slurry is about 65% by weight) is provided. Specifically, the PVA is a polyvinyl alcohol having a hydrolysis level of about 88% and a degree of polymerization of about 1700, which is commercially available from Sigma Aldrich. The DEEDMAC is commercially available under the tradename Rewoquat from Evonik Industries. The PMC slurry may contain a first type of PMCs having shells of melamine cross-linked with formaldehyde and cationic coatings of polyvinylformamide formed thereover ("HEPMC"), which is commercially available from Encapsys (Appleton, WI). Alternatively, the PMC slurry may contain a second type of PMCs having shells of polyacrylates without any coating ("PAC PMC"), which is also commercially available from Encapsys (Appleton, WI).

The method of wet pre-mixture preparation is as follows:
1. Water and glycerin are firstly added together into a glass beaker and stirred at 200 rpm using an overhead stirrer.
2. While continuing to stir, the PVA is then slowly added into the beaker containing water and glycerin, ensuring that no foaming of the solution or clumping of the PVA occurred.
3. The beaker is then placed in a water bath and heated to 80° C. while continuing stirring. The beaker is covered with clingfilm or tinfoil in order to mitigate water evaporation and left to continue mixing for at least 1.0 hour.
4. The remaining components (e.g., the PMC slurry, DEEDMAC, starch, etc.) are weighed and added together in a separate glass beaker. The balance of water required to achieve 65% total water content in the slurry is also added to this beaker.
5. This beaker is placed in a water bath at 80° C., and its contents are stirred using an overhead stirrer at 500 rpm for at least 30 minutes.
6. Once the predefined mixing time is reached in both beakers, the contents of both are added together into a single glass beaker, followed by continued stirring at 500 rpm and the temperature is maintained at 80° C. for at least another 30 minutes.

The wet pre-mixture so formed has a viscosity of about 19254.6 cps. It is then aerated as follows:
1. An Aeros A20 continuous aerator, consisting of a jacketed hopper (model JCABT10) and A20 mixing head, is preheated to 80° C. using a water bath and pump.
2. The slurry prepared previously is then added to the hopper. The aerator unit is then switched on and the mixing head speed, feed pump speed, and air flow rates were set to 600, 500 and 100 respectively.
3. The aerated slurry is collected from the aerator outlet and its density measured by filling a density cup of known volume and weighing the mass of the aerated slurry.

At the aerator settings described above, an aerated slurry density of about 0.225 g/cm$^3$ is achieved.

Flexible and porous solid sheets of about 0.8-1.5 mm in thickness are produced using a rotary drum dryer process, as follows:
1. The rotary drum dryer (having a drum diameter of about 1.5 m) is pre-heated to about 100° C.
2. The aerated slurry collected from the Aeros A20 outlet is added to the feeding trough of the drum dryer.
3. Once added, the rotation of the drum dryer starts and is set at a rotating speed so that the slurry residence time on the heated drum is about 15 minutes.
4. Once dried, the flexible and porous sheets so formed are peeled from the drum surface and placed in a plastic bag.

Then, the solid sheets with Direct-Added HEPMCs or PAC PMCs are stored under ambient relative humidity of 50±2% and temperature of 23±1° C. for 24 hours (i.e., a conditioning step). The average thickness of all the Sheet 1 is 1.2107 mm with a standard deviation of 0.0464.

2) Preparation of Solid Sheet Articles with Post-Added PMCs

Flexible, porous and dissolvable solid sheet articles containing the Post-Added PMCs are prepared as follows.

Specifically, a wet pre-mixture containing 9.85% of PVA, 10.1% of DEEDMAC, 13.77% of glycerin, 1.33% of starch, and a balance of water to result in a total solids content of about 35% by weight (i.e., the total water content in the slurry is about 65% by weight) is provided.

The method of wet pre-mixture preparation is as follows:
1. Water and glycerin are firstly added together into a glass beaker and stirred at 200 rpm using an overhead stirrer.
2. While continuing to stir, the polyvinyl alcohol is then slowly added into the beaker containing water and glycerin, ensuring that no foaming of the solution or clumping of the polyvinyl alcohol occurred.
3. The beaker is then placed in a water bath and heated to 80° C. while continuing stirring. The beaker is covered with clingfilm or tinfoil in order to mitigate water evaporation and left to continue mixing for at least 1.0 hour.
4. The remaining components (e.g., DEEDMAC, starch, etc.) are weighed and added together in a separate glass beaker. The balance of water required to achieve 65% total water content in the slurry is also added to this beaker.
5. This beaker is placed in a water bath at 80° C., and its contents are stirred using an overhead stirrer at 500 rpm for at least 30 minutes.
6. Once the predefined mixing time is reached in both beakers, the contents of both are added together into a single glass beaker, followed by continued stirring at 500 rpm and the temperature is maintained at 80° C. for at least another 30 minutes.

The wet pre-mixture so formed has a viscosity of about 19254.6 cps. It is then aerated as follows:
4. An Aeros A20 continuous aerator, consisting of a jacketed hopper (model JCABT10) and A20 mixing head, is preheated to 80° C. using a water bath and pump.
5. The slurry prepared previously is then added to the hopper. The aerator unit is then switched on and the mixing head speed, feed pump speed, and air flow rates were set to 600, 500 and 100 respectively.
6. The aerated slurry is collected from the aerator outlet and its density measured by filling a density cup of known volume and weighing the mass of the aerated slurry.

At the aerator settings described above, an aerated slurry density of about 0.225 g/cm$^3$ is achieved.

Flexible and porous solid sheets of about 0.8-1.5 mm in thickness are produced using a rotary drum dryer process, as follows:
5. The rotary drum dryer (having a drum diameter of about 1.5 m) is pre-heated to about 130° C.
6. The aerated slurry collected from the Aeros A20 outlet is added to the feeding trough of the drum dryer.
7. Once added, the rotation of the drum dryer starts and is set at a rotating speed so that the slurry residence time on the heated drum is about 15 minutes.
8. Once dried, the flexible and porous sheets so formed are peeled from the drum surface and placed in a plastic bag.

Then, the solid sheets are stored under ambient relative humidity of 50±2% and temperature of 23±1° C. for 24 hours (i.e., a conditioning step). The average thickness of all the Sheet 1 is 1.2107 mm with a standard deviation of 0.0464.

Subsequently, 0.352 grams of a PMC slurry containing 32.25% HEPMCs or PAC PMCs and 67.75% water is applied in between solid sheets. The solid sheets with such Post-Added HEPMCs or PAC PMCs are then stored for another 24 hours at the same humidity and temperature conditions (50±2% and 23±1° C.).

The flexible, porous, dissolvable solid sheets as made by the above processes, with either Direct-Added or Post-Added HEPMCs or PAC PMCs, are then tested using the Hand Dissolution Method described hereinabove in Test 9. The sheet formulations and the respective hand dissolution test results are provided hereinafter:

TABLE 1

(DRY SHEET FORMULATIONS)

| Ingredients (wt %) | Sheet A (with Direct-Added HEPMC) | Comparative Sheet 1 (with Post-Added HEPMC) | Sheet B with (Direct-Added PAC PMC) | Comparative Sheet 2 (with Post-Added PACP MC) |
|---|---|---|---|---|
| PVA | 24.7 | 24.7 | 24.7 | 24.7 |
| DEEDMAC | 25.4 | 25.4 | 25.4 | 25.4 |
| Glycerin | 34.6 | 34.6 | 34.6 | 34.6 |
| PMC | 2 | 2 | 2 | 2 |
| Starch | 3.34 | 3.3 | 3.3 | 3.3 |
| Water Content | Balance | Balance | Balance | Balance |
| Hand Dissolution (# of strokes) | 7-8 | 30 | 7-8 | 30 |

The above data shows that the flexible, porous, dissolvable solid sheets containing Direct-Added PMCs (either HEPMC or PAC PMC) have significantly improved dissolution profile in comparison with similar solid sheets containing Post-Added PMCs.

Example 2: Comparative Long-Lasting Freshness of Solid Sheet Articles Containing Direct-Added PMCs and Those Containing Post-Added PMCs Flexible, porous, dissolvable solid sheets containing either Direct-Added PAC PMCs or Post-Added PAC PMCs are made by similar processing steps as in Example 1. Such solid sheets are then tested using the Long-Lasting Freshness Method described hereinabove in Test 10. The sheet formulations and the respective freshness test results are provided hereinafter:

TABLE 2

(DRY SHEET FORMULATIONS)

| Ingredients (wt %) | Sheet C (with Direct-Added PMC) | Comparative Sheet 3 (with Post-Added PMC) |
|---|---|---|
| PVA | 24.7 | 24.7 |
| DEEDMAC | 25.4 | 25.4 |
| Glycerin | 34.6 | 34.6 |
| PAC PMC | 2 | 2 |
| Starch | 3.3 | 3.3 |
| Water Content | Balance | Balance |

TABLE 3

(LONG-LASTING FRESHNESS RESULTS)

| | Without Rubbing | With Rubbing |
|---|---|---|
| Overall Freshness Score [a] | 1 | 2 |

[a] The scores are given by each panelist as follows: "0" means "Sheets C and 3 are the same"; "1" means "Sheet C seems better than Sheet 3, but not sure"; "2" means "Sheet C is slightly better than Sheet 3"; and "3" means "Sheet C is significantly better than Sheet 3."

The above data shows that a flexible, porous, dissolvable solid sheet containing a lower dosage of Direct-Added PMCs exhibits a comparable long-lasting freshness benefit as a similar solid sheet containing a higher dosage of Post-Added PMCs when the test fabrics are unrubbed, while an even better long-lasting freshness benefit when the test fabrics are rubbed. This result is surprising and unexpected, especially contrary to convention wisdom.

Example 4: Exemplary Solid Sheet Articles with Direct-Added Microcapsules

The following are examples of flexible, porous, dissolvable solid sheet articles containing Direct-Added microcapsules, which are made by similar processing steps as in Example 1. Some of the sheets may further contain a coating composition containing perfumes, nonionic surfactants, and/or solvents (e.g., dipropylene glycol) on a surface thereof.

| Ingredients (w/w %) | D | E | F | G | H | I | J | K | L | M |
|---|---|---|---|---|---|---|---|---|---|---|
| Polyvinyl Alcohol (with a degree of polymerization of about 1700) | 21 | 23.69 | 18 | 21 | 23.5 | 11.52 | 10.98 | 28.1 | 20 | 20 |
| Polyvinyl Alcohol (with a degree of polymerization of about 500) | — | — | 6 | — | — | 3.84 | 3.66 | — | — | — |
| Glycerin | 3 | 9.51 | 3.5 | 3 | 9.4 | 2.25 | 2.14 | 9.6 | 9 | 9 |
| Linear Alkylbenzene Sulfonate | 53 | — | 40 | — | — | 25.6 | 24.4 | — | 41.77 | — |
| Sodium Lauryl Sulfate | — | 32.89 | — | — | — | — | — | — | — | — |
| Sodium Laureth-1 Sulfate | — | — | — | — | 38.5 | — | — | — | — | — |
| Sodium Laureth-3 Sulfate | 10 | 10.42 | 4.6 | 10 | 4.4 | 2.94 | 2.81 | — | 12 | — |
| C12-C14 Ethoxylated Alcohol (average EO 7 or 9) | 10 | — | 16 | 10 | — | 32.56 | 31.52 | — | — | — |
| C10-C16 Alkyl Ether Sulfate (average EO 0.6) | — | — | — | — | — | — | — | — | — | 43.92 |

-continued

| Ingredients (w/w %) | D | E | F | G | H | I | J | K | L | M |
|---|---|---|---|---|---|---|---|---|---|---|
| Sodium Lauroamphoacetate | — | 17.28 | — | — | 17.1 | — | — | 11.3 | — | — |
| Sodium Trideceth Sulfates with a weight average degree of ethoxylation of about 2 ($ST_2S$) | — | — | — | 53 | — | — | — | — | — | — |
| Sodium Lauraimidopropyl Betaine | — | — | — | — | — | — | — | 28.1 | — | — |
| Lauramine Oxide | — | — | — | — | — | — | — | — | — | 9.85 |
| Sodium Lauroyl Methyl Isethionate | — | — | — | — | — | — | — | 16.9 | — | — |
| Ethoxylated Polyethyleneimine | — | — | 1.5 | — | — | 0.96 | 0.92 | — | 2 | 2 |
| Guar Hydroxypropyltrimonium Chloride | — | — | — | — | 1.2 | — | — | — | — | — |
| Fatty acids or salts thereof | — | — | 2.07 | — | — | 1.32 | 1.26 | — | 2 | 2 |
| Citric Acid | — | 3.21 | — | — | 2.9 | — | — | — | — | — |
| PMC | 1 | 1 | 1 | 2 | 2 | 2 | 3 | 3 | 5 | 5 |
| Neat perfumes | — | — | — | — | — | 13.68 | 13.33 | — | — | — |
| Zeolite | — | — | 0.95 | — | — | 0.61 | 0.58 | — | 1 | 1 |
| Dipropylene Glycol | — | — | — | — | — | — | 3.9 | — | — | — |
| Denatonium Benzoate | — | — | 0.04 | — | — | 0.03 | 0.02 | — | — | — |
| Water | Q.S. | Q.S. | Q.S. | Q.S. | Q.S. | Q.S. | Q.S. | Q.S. | Q.S | Q.S |

| Ingredients (w/w %) | N | O | P | Q | R | S |
|---|---|---|---|---|---|---|
| Polyvinyl Alcohol (with a degree of polymerization of about 1700) | 20 | 25.3 | 22.3 | 24.7 | 25 | 25 |
| Polyvinyl Alcohol (with a degree of polymerization of about 500) | — | — | — | — | — | — |
| Glycerin | 20 | 35.4 | 34.4 | 34.6 | 33.8 | 34.7 |
| C12-C14 Ethoxylated Alcohol | 25.1 | — | — | — | — | — |
| DEEDMAC | — | 25.9 | — | 25.4 | 20 | 23 |
| HTQ | — | — | 31.1 | — | — | — |
| Ethanaminium, 2-hydroxy-N-(2-hydroxyethyl)-N,N-dimethyl-, esters with C16-18 and C18-unsatd. fatty acids, chlorides | 25 | — | — | — | — | — |
| Lauryl trimethyl ammonium chloride | — | — | — | — | 5 | 2 |
| Starch | — | 3.4 | 2.2 | 3.3 | 2.5 | 3.3 |
| Silica | — | — | — | — | 2.5 | — |
| 2-Propanol | 2.8 | — | — | — | — | — |
| Citric Acid | 4.1 | — | — | — | — | — |
| PMC | 0.1-12 | 0.2-8 | 1-5 | 2 | 2 | 2 |
| Water | Q.S. | Q.S. | Q.S. | Q.S. | Q.S. | Q.S |

| Ingredients (w/w %) | T | U | V |
|---|---|---|---|
| Polyvinyl Alcohol (with a degree of polymerization of about 1700) | 21.7 | 21.7 | 22.91 |
| Glycerin | 8.07 | 8.07 | 7.81 |
| Sodium Lauryl Sulfate | 32.61 | — | — |
| Sodium Laureth-3 Sulfate | 8.86 | — | — |
| Sodium Laureth-1 Sulfate | — | 41.46 | — |
| Sodium Lauroyl Methyl Isethionate | — | — | 22.65 |
| Sodium lauramidopropyl betaine | — | — | 7.17 |
| Sodium Cocoyl Isethionate | — | — | 10.61 |
| Sodium Cocoyl Glutamate, Disodium Cocoyl Glutamate | — | — | 10.61 |
| Sodium Lauroamphoacetate | 9.96 | 9.96 | — |
| Guar Hydroxypropyltrimonium Chloride | 0-2 | 0-2 | 0-2 |
| Polyquat-76 | 0-0.2 | 0-0.2 | 0-0.2 |
| Citric Acid | 1-2 | 1-2 | 1-2 |
| Sodium Benzoate | 0.3-0.5 | 0.3-0.5 | 0.3-0.5 |
| PMC | 2-5 | 2-5 | 2-5 |
| Neat perfumes | 1-8 | 1-8 | 1-8 |
| Water | Q.S. | Q.S. | Q.S. |

| Ingredients (w/w %) | W | X | Y |
|---|---|---|---|
| Polyvinyl Alcohol (with a degree of polymerization of about 1700) | 23 | 26.5 | 26.5 |
| Glycerin | 20.5 | 20 | 10 |
| Lauryl trimethyl ammonium chloride | 18 | — | 5 |
| DEEDMAC | 4 | — | 5 |
| Disodium Cocoyl Glutamate | — | 7 | — |
| Amine oxide | — | 7 | — |
| Cationically modified hydroxyethyl cellulose | 5 | — | — |
| Starch | 1.5 | 1.5 | 1.5 |
| PMC | 20 | 30 | 44 |
| Water | Q.S. | Q.S. | Q.S. |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document

What is claimed is:

1. A process for preparing a solid sheet article, comprising:
    a) providing a wet pre-mixture comprising a water-soluble polymer, a surfactant and polyacrylate microcapsules, wherein said wet pre-mixture has a viscosity of from about 1,000 cps to about 25,000 cps measured at 40° C. and 1 s−1, wherein each of said microcapsules comprises a core and a shell at least partially surrounding the core, and wherein the core comprises a benefit agent; and
    b) aerating said wet pre-mixture to form an aerated wet pre-mixture having a density of from about 0.05 to about 0.5 g/ml; and
    c) forming said aerated wet pre-mixture into a sheet; and
    d) drying said formed sheet for a drying time of from about 1 minute to about 60 minutes at a temperature from about 140° C. to about 200° C. to form said solid sheet article, wherein a heating direction is offset from a gravitational direction by at least 90 degrees.

2. The process of claim 1, wherein the benefit agent in the core of each of said microcapsules comprises perfume, silicone oil, wax, hydrocarbon, higher fatty acid, essential oil, lipid, skin coolant, vitamin, sunscreen, antioxidant, glycerin, catalyst, bleach particle, silicone dioxide particle, malodor reducing agent, odor-controlling material, chelating agent, antistatic agent, softening agent, insect and moth repelling agent, colorant, bodying agent, drape and form control agent, smoothness agent, wrinkle control agent, sanitization agent, disinfecting agent, germ control agent, mold control agent, mildew control agent, antiviral agent, drying agent, stain resistance agent, soil release agent, fabric refreshing agent, freshness extending agent, chlorine bleach odor control agent, dye fixative, dye transfer inhibitor, color maintenance agent, optical brightener, color restoration/rejuvenation agent, anti-fading agent, whiteness enhancer, anti-abrasion agent, wear resistance agent, fabric integrity agent, anti-wear agent, deformer, anti-foaming agent, UV protection agent, sun fade inhibitor, anti-allergic agent, enzyme, water-proofing agent, fabric comfort agent, shrinkage resistance agent, stretch resistance agent, stretch recovery agent, skin care agent, natural active, antibacterial active, antiperspirant active, cationic polymer, dye, or a combination thereof.

3. The process of claim 2, wherein the benefit agent in the core of each of said microcapsules comprises perfume.

4. The process of claim 1, wherein said surfactant in the wet pre-mixture comprises an anionic surfactant, nonionic surfactant, cationic surfactant, zwitterionic surfactant, amphoteric surfactant, polymeric surfactant, or a combination thereof.

5. The process according to claim 1, wherein the surfactant in the wet pre-mixture comprises one or more Group I surfactants and one or more Group II surfactants, wherein the Group I surfactants are anionic surfactants, wherein the Group II surfactants are selected from the group consisting of amphoteric surfactants, zwitterionic surfactants, and combinations thereof.

6. The process according to claim 5, wherein the ratio by weight of Group I to Group II surfactants is from about 5:95 to about 30:70.

7. The process according to claim 5, wherein the ratio by weight of Group I to Group II surfactants is from about 40:60 to about 85:15.

8. The process according to claim 5, wherein the ratio by weight of Group I to Group II surfactants is from about 55:45 to about 70:30.

9. The process according to claim 1, wherein the surfactant in the wet pre-mixture comprises a diester quaternary ammonium (DEQA) compound, a $C_{12}$-$C_{22}$ mono/di-alkyl quaternary ammonium compound, a $C_{12}$-$C_{22}$ mono-alkyl amine compound, a $C_8$-$C_{18}$ alkyl ethoxylated alcohol having a weight average degree of ethoxylation from about 1 to about 20, or a combination thereof; and wherein each of said microcapsules further comprises a cationic coating over its shell, wherein said cationic coating is formed of a cationic polymer comprising polyvinylformamide, partially hydroxylated polyvinylformamide, polyvinylamine, polyethyleneimine, ethoxylated polyethyleneimine, cationically modified polysaccharide, or a combination thereof.

10. The process according to claim 1, wherein the surfactant in the wet pre-mixture comprises a $C_6$-$C_{20}$ linear alkylbenzene sulfonate (LAS), a $C_6$-$C_{20}$ linear or branched alkylalkoxy sulfate (AAS) having a weight average degree of alkoxylation ranging from about 0.5 to about 10, a $C_6$-$C_{20}$ linear or branched alkyl sulfate (AS), a $C_6$-$C_{20}$ linear or branched alkylalkoxylated alcohol (AA) having a weight average degree of alkoxylation ranging from about 5 to about 15, or a combination thereof; and wherein the shell of each of said microcapsules comprises an anionic polymer comprising poly(meth)acrylate, polyvinyl(meth)acrylate, poly(ethylene-maleic anhydride), or a combination thereof.

* * * * *